United States Patent
O'Keefe et al.

(10) Patent No.: US 9,335,298 B2
(45) Date of Patent: *May 10, 2016

(54) WEAR MONITORING WITH ROTATIONAL SENSOR AND SENSOR THICKNESS

(71) Applicant: CiDRA Corporate Services Inc., Wallingford, CT (US)

(72) Inventors: Christian Victor O'Keefe, Durham, CT (US); Robert J. Maron, Middletown, CT (US); Mark R. Fernald, Enfield, CT (US); Timothy J. Bailey, Longmeadow, MA (US); Alex M. Van der Spek, Rotterdam (NL); Michael A. Davis, Glastonbury, CT (US); John V. Viega, Ellington, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/953,254

(22) Filed: Jul. 29, 2013

(65) Prior Publication Data

US 2014/0026666 A1 Jan. 30, 2014

Related U.S. Application Data

(63) Continuation of application No. 12/922,261, filed as application No. PCT/US2009/037269 on Mar. 16, 2009.

(60) Provisional application No. 61/133,878, filed on Jul. 2, (Continued)

(51) Int. Cl.
*G01N 29/24* (2006.01)
*G01N 29/04* (2006.01)
*G01B 17/02* (2006.01)

(52) U.S. Cl.
CPC ............... *G01N 29/04* (2013.01); *G01B 17/02* (2013.01); *G01N 29/2437* (2013.01)

(58) Field of Classification Search
CPC . G01N 29/043; G01N 29/06; G01N 29/0618; G01N 29/0645; G01N 29/069; G01N 29/07; G01N 29/22; G01N 29/223; G01N 29/2437; G01N 29/2443; G01N 29/245; G01N 29/4418; G01N 2291/0232; G01N 2291/0234; G01N 2291/02854; G01N 2291/0289; G01N 2291/044; G01N 2291/106; G01N 2291/2634
USPC .................... 73/622, 624, 625, 626, 628, 637
See application file for complete search history.

(56) References Cited

U.S. PATENT DOCUMENTS 4,052,887 A   10/1977  Sheridan et al.
4,217,782 A    8/1980  Pont
(Continued)

FOREIGN PATENT DOCUMENTS

WO    WO 2005047817 A1 *  5/2005

OTHER PUBLICATIONS

D.L. Gysling and E. Mueller, "Application of Sonar-Based, Clamp-on Flow Meter in Oilsand Processing" Presented at ISA 2004 Exhibit and Conference—Edmonton Section, Apr. 2004.
(Continued)

*Primary Examiner* — John Fitzgerald
*Assistant Examiner* — Rose M Miller

(57) ABSTRACT

Apparatus for determining a thickness of a wall of a pipe, featuring a signal processing module configured to respond to signaling containing information about traveling stress waves transmitted to and reflected back from a wall of a pipe by a sensor band that includes a series, ring or array having multiple transducers circumferentially arranged and mounted around, and attached to or clamped onto, an outside wall of the pipe; and determine a profile of a thickness of the wall of the pipe corresponding to circumferential locations of the multiple transducers based on the signaling received from the sensor band; and one or more orientation or rotation sensors, each responding to its orientation in relation to its displacement on the pipe and to provide an orientation signal containing information about the same.

31 Claims, 29 Drawing Sheets

Related U.S. Application Data 2008, provisional application No. 61/103,686, filed on Oct. 8, 2008, provisional application No. 61/117,762, filed on Nov. 25, 2008, provisional application No. 61/036,689, filed on Mar. 14, 2008, provisional application No. 61/054,612, filed on May 20, 2008.

(56) References Cited

U.S. PATENT DOCUMENTS

| | | | |
|---|---|---|---|
| 4,375,165 | A | 3/1983 | de Sterke |
| 4,578,442 | A * | 3/1986 | Ohigashi et al. ............... 526/255 |
| 4,718,277 | A | 1/1988 | Glascock |
| 4,843,884 | A | 7/1989 | House et al. |
| 4,881,409 | A | 11/1989 | Roarty |
| 5,007,291 | A | 4/1991 | Walters et al. |
| 5,156,636 | A | 10/1992 | Kuljis |
| 5,303,592 | A | 4/1994 | Livingston |
| 5,415,045 | A | 5/1995 | Wadaka et al. |
| 5,471,880 | A | 12/1995 | Lang et al. |
| 5,482,044 | A | 1/1996 | Lin et al. |
| 5,549,004 | A | 8/1996 | Nugent |
| 6,377,654 | B1 | 4/2002 | Willems et al. |
| 6,904,818 | B2 | 6/2005 | Harthorn et al. |
| 7,194,907 | B2 | 3/2007 | Abbate et al. |
| 7,328,618 | B2 | 2/2008 | Hunaidi et al. |
| 2003/0004415 | A1 * | 1/2003 | Satoh ............................ 600/443 |
| 2004/0187582 | A1 * | 9/2004 | Satoh ............................ 73/606 |
| 2006/0266121 | A1 * | 11/2006 | Leybovich ..................... 73/597 |
| 2007/0004457 | A1 | 1/2007 | Han |
| 2007/0044571 | A1 | 3/2007 | Gysling et al. |
| 2007/0279235 | A1 | 12/2007 | Davis et al. |
| 2008/0000299 | A1 * | 1/2008 | Georgeson ..................... 73/606 |
| 2008/0178678 | A1 | 7/2008 | Girndt |
| 2008/0236286 | A1 * | 10/2008 | Lam et al. ...................... 73/618 |

OTHER PUBLICATIONS

2 Pages PCT/US2009/037269 International Search Report mailed Jun. 4, 2009.

* cited by examiner

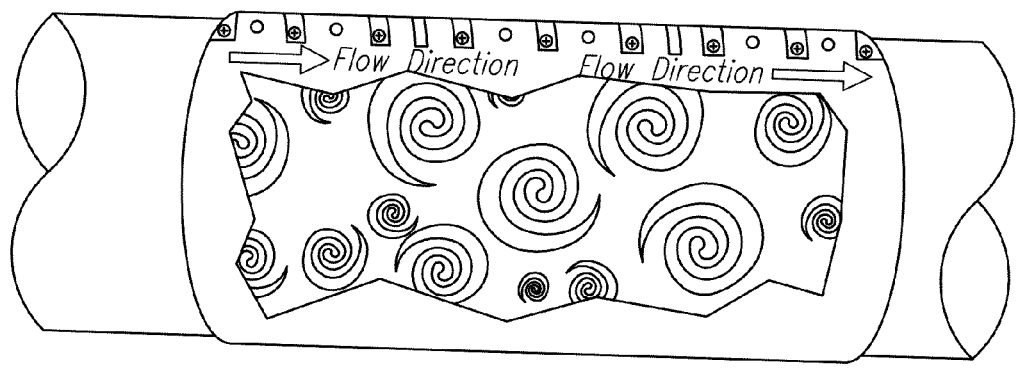
FIG. 1: Cutaway of pipe under sonar array sensor band illustrating turbulent eddies

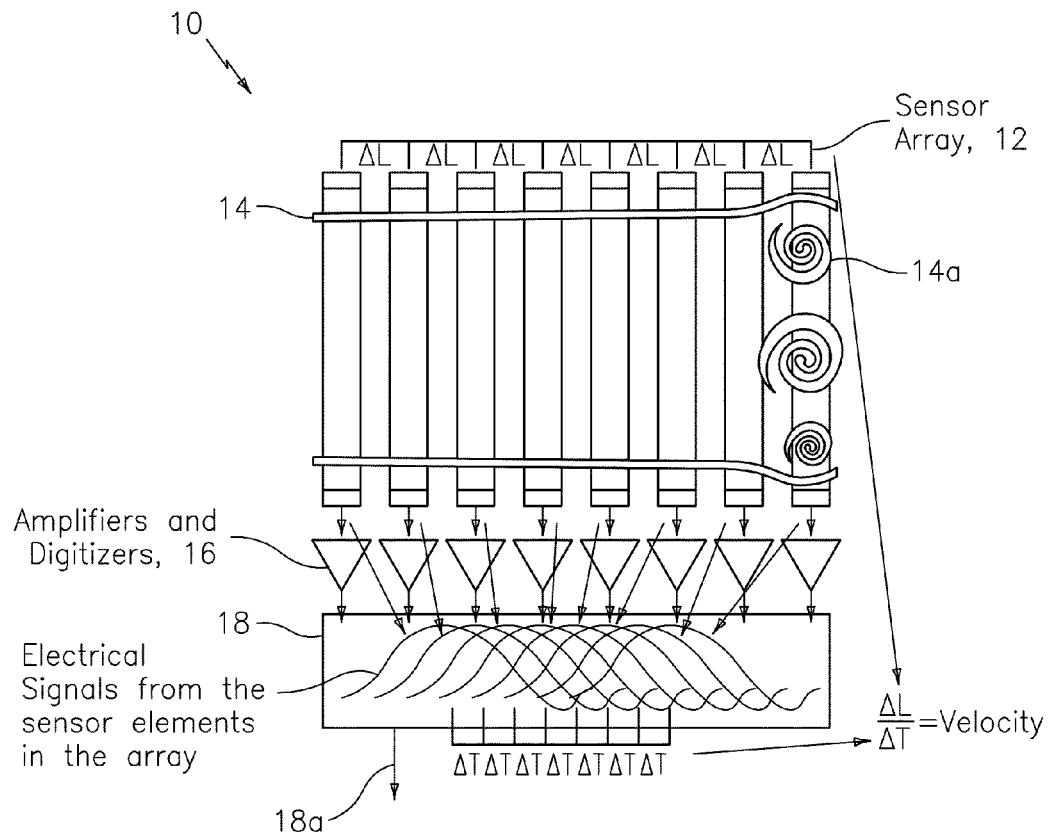
FIG. 2: Illustration of signal detected by passive sensors in array from one collection of turbulent eddies

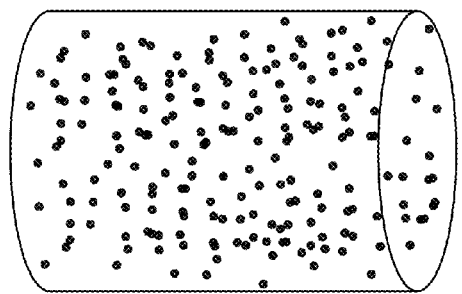
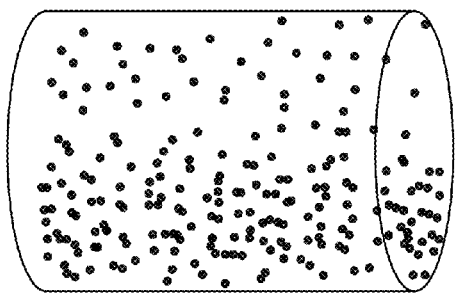
FIG. 3a          FIG. 3b
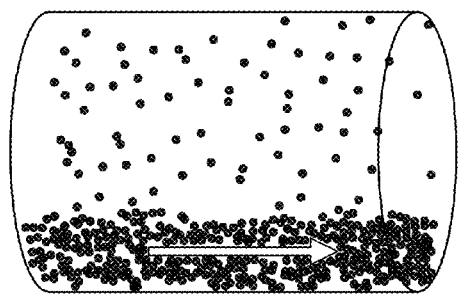
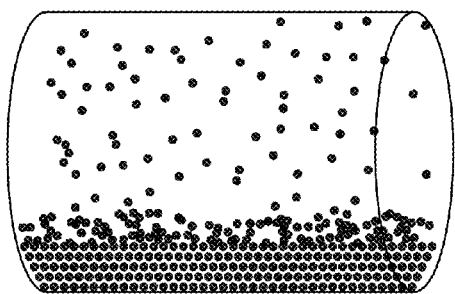
FIG. 3c          FIG. 3d
FIG. 3: (Top Left) Homogeneous flow;
(Top Right) Heterogeneous flow—full suspended particles;
(Bottom Left) Heterogeneous flow—moving bed;
(Bottom Right) Heterogeneous flow—stationary bed.

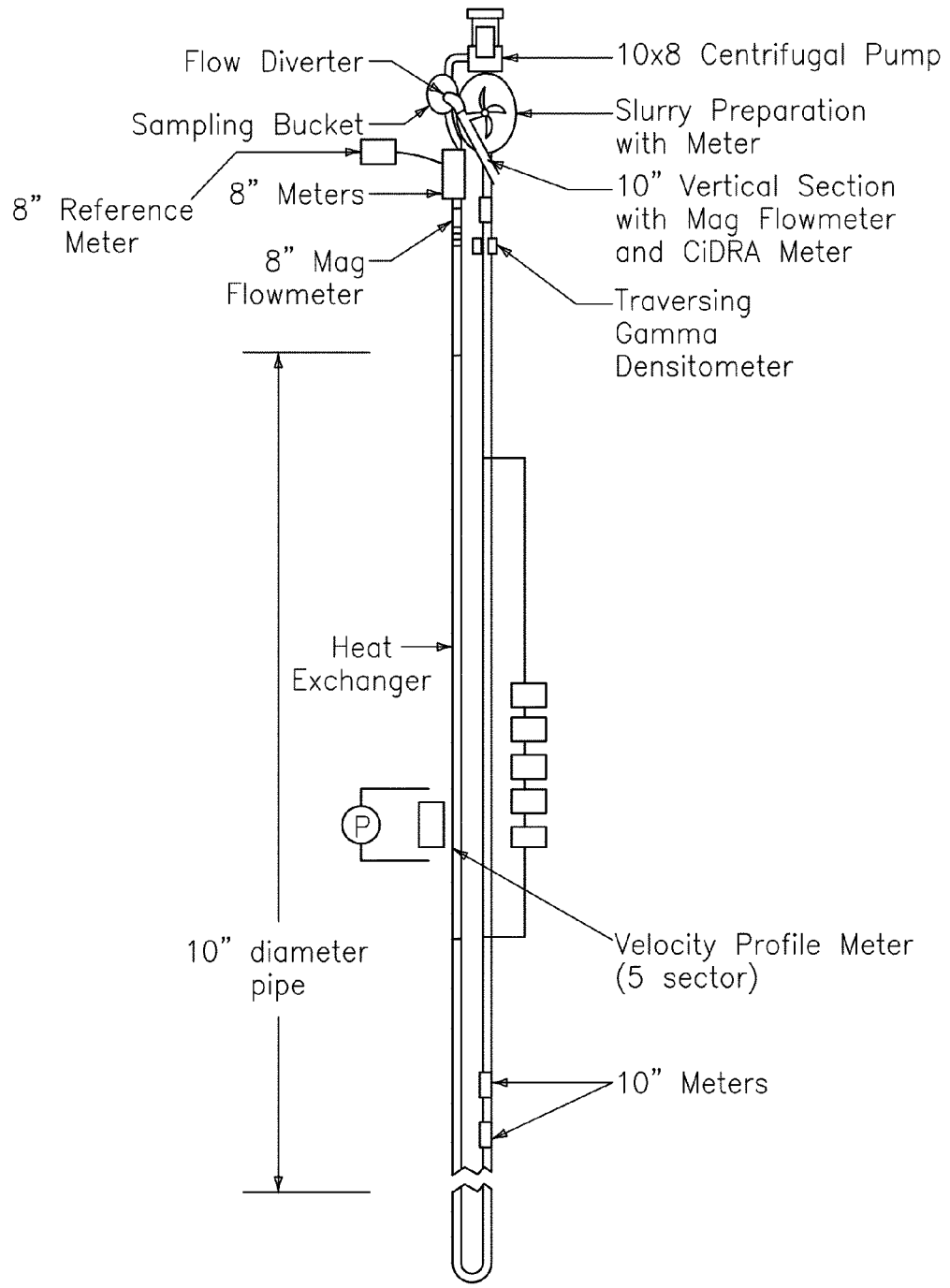
FIG. 4: Test loop setup

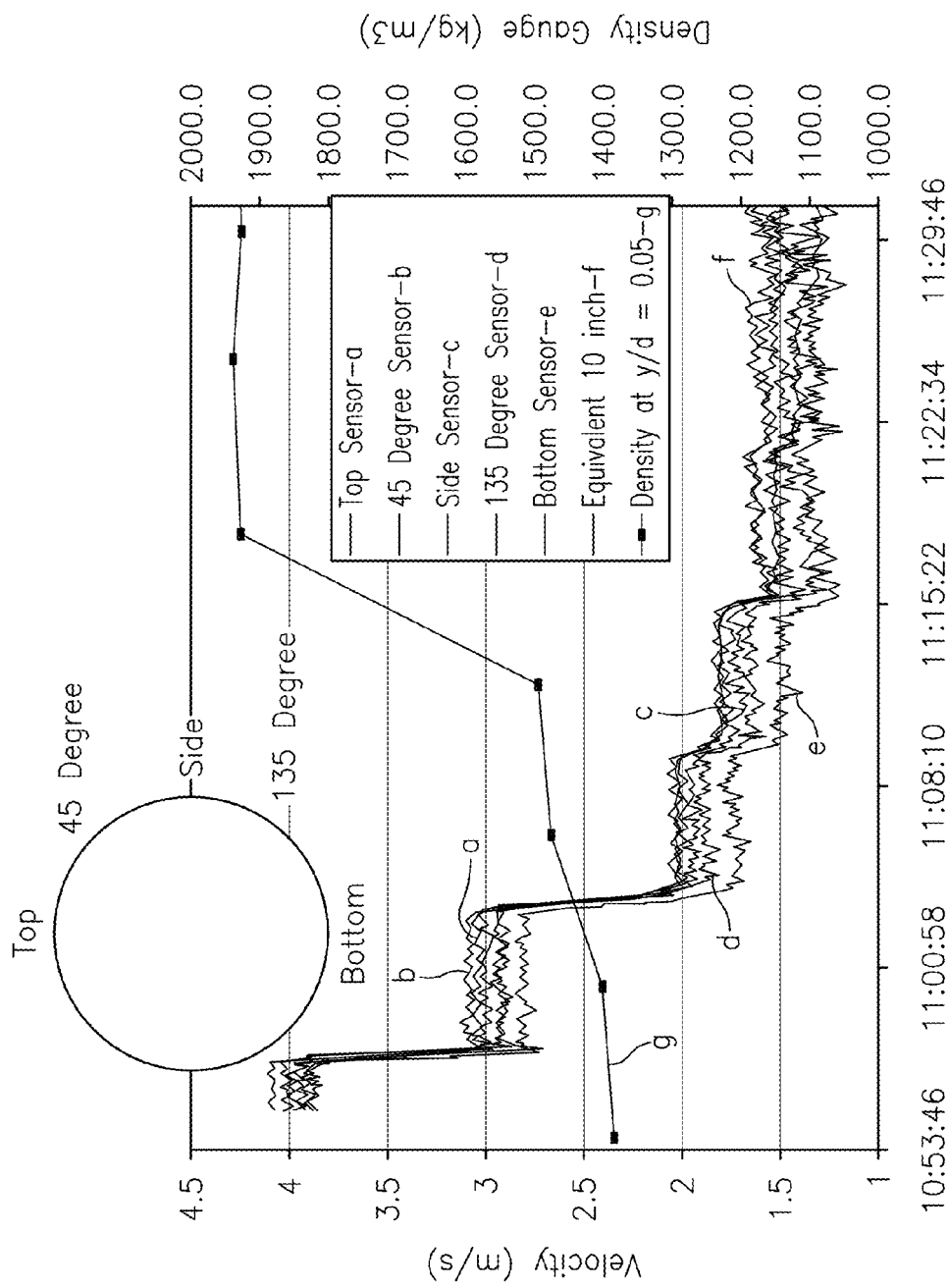
FIG. 5: Velocity profile of 89 μm mining slurry.

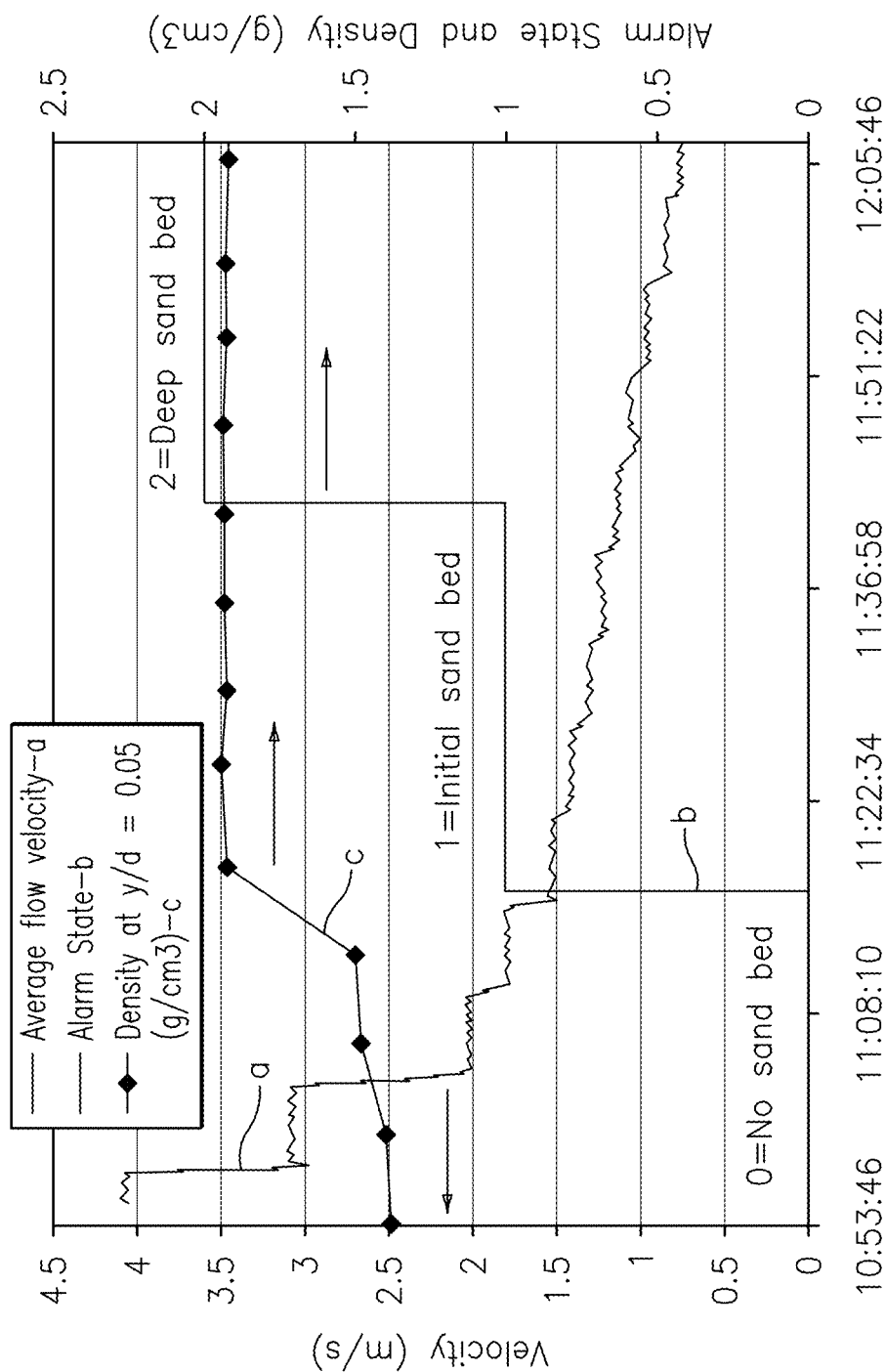
FIG. 6: Alarm States – 89 μm slurry.

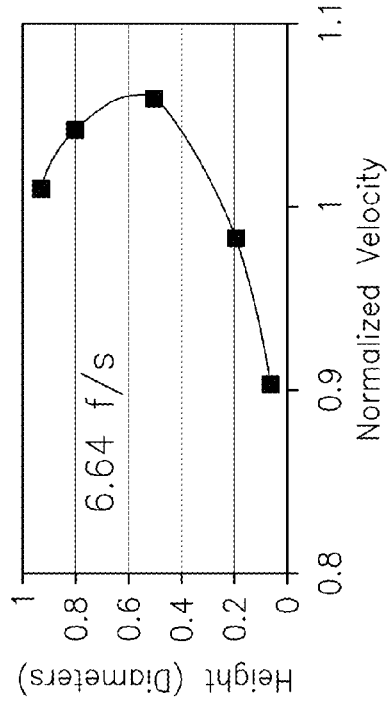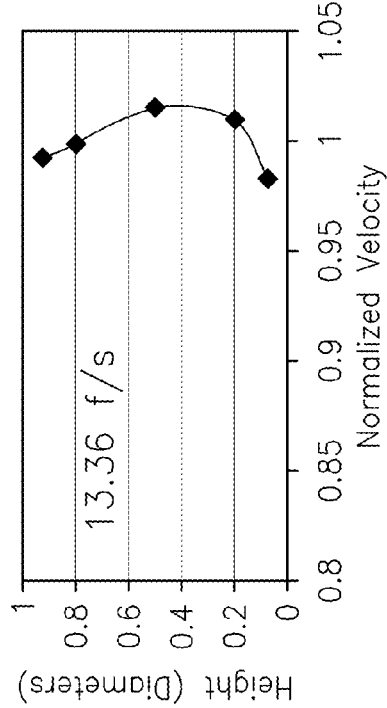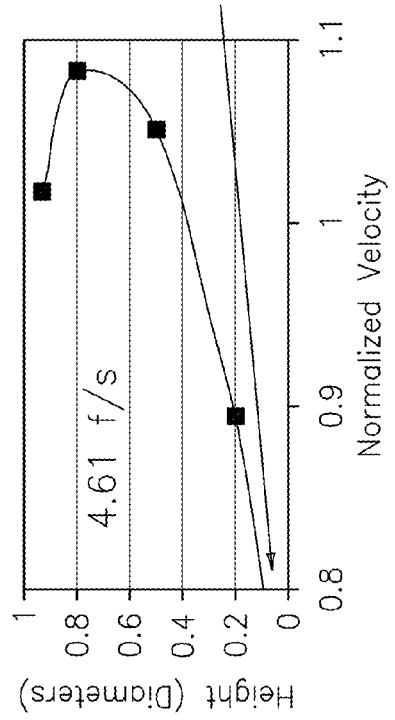
FIG. 7: (Left) Mostly homogeneous flow, suspended particles and (Right) Heterogeneous flow, suspended particles
FIG. 8: Heterogeneous flow, stationary solids bed

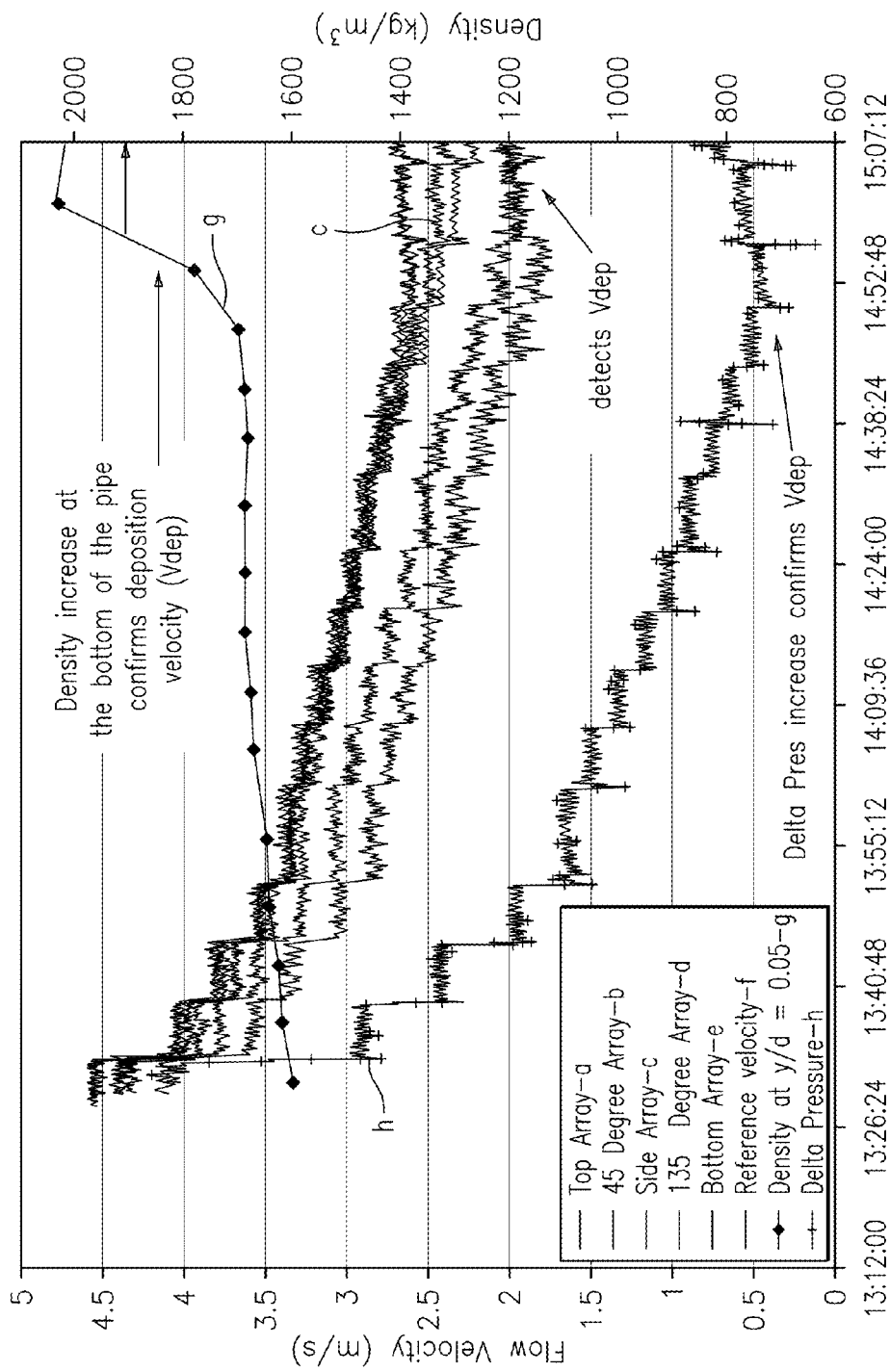
FIG. 9: 186 μm Slurry solid deposition detected by sonar meter, densitometer, and delta-pressure

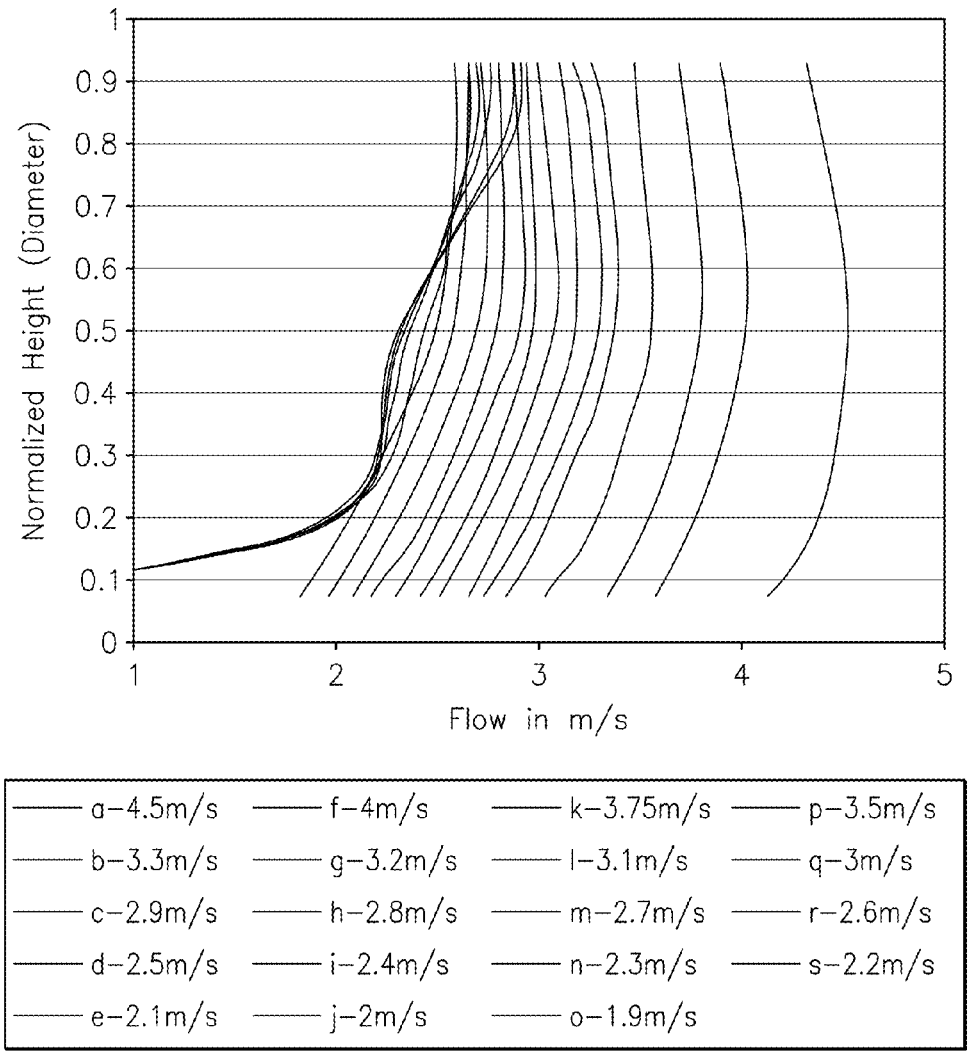
*FIG. 10*: Velocity profiles vs. reference velocity

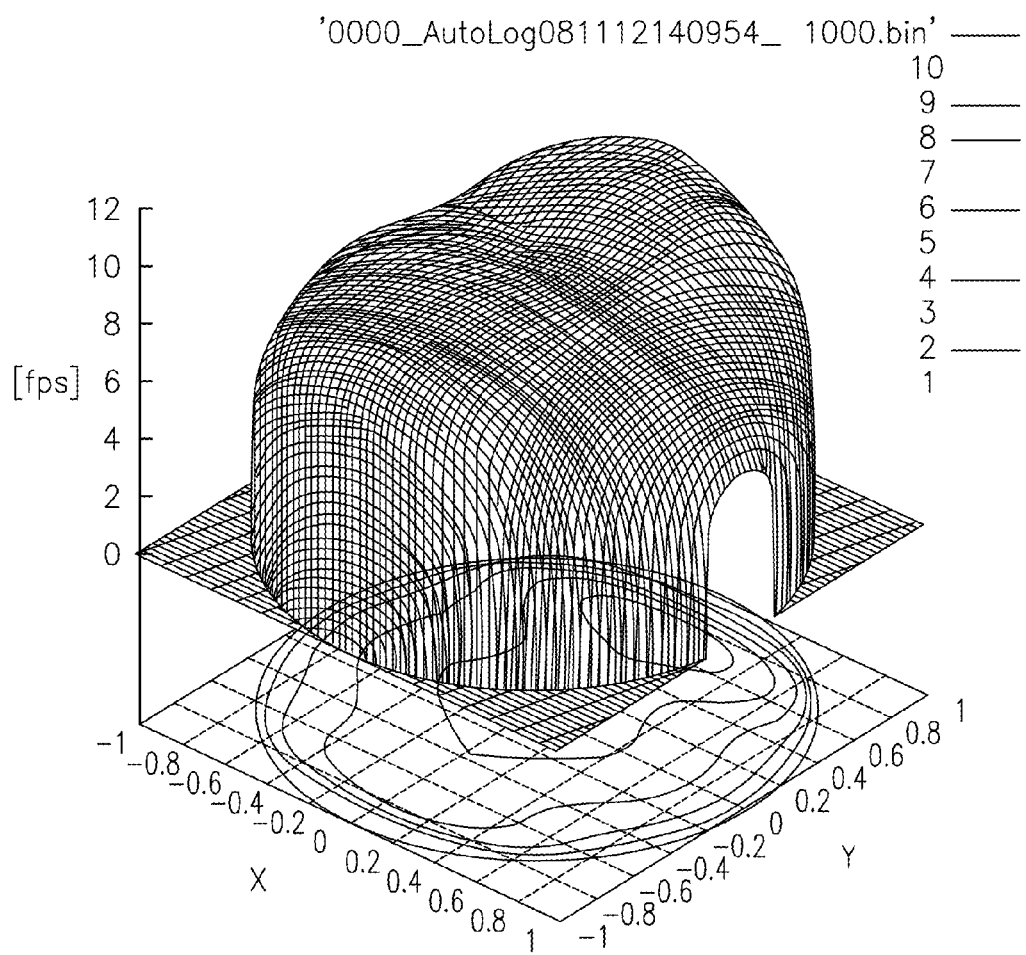
*FIG. 11*: Three-dimensional velocity profiles and velocity contours in an inhomogeneous flow FIG. 12: Operation of velocity profile monitoring system at site.

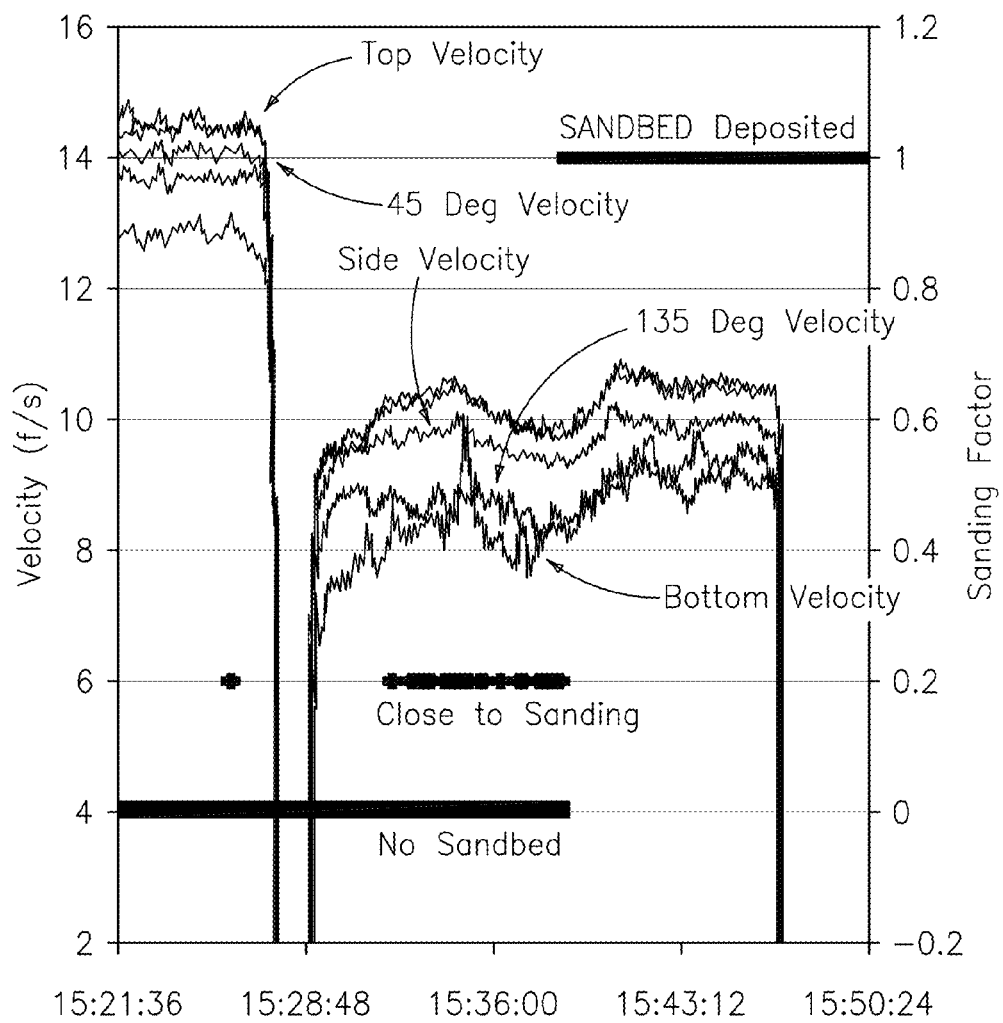
FIG. 13: Detection of sand bed and development of sand bed in slurry pipeline in the field

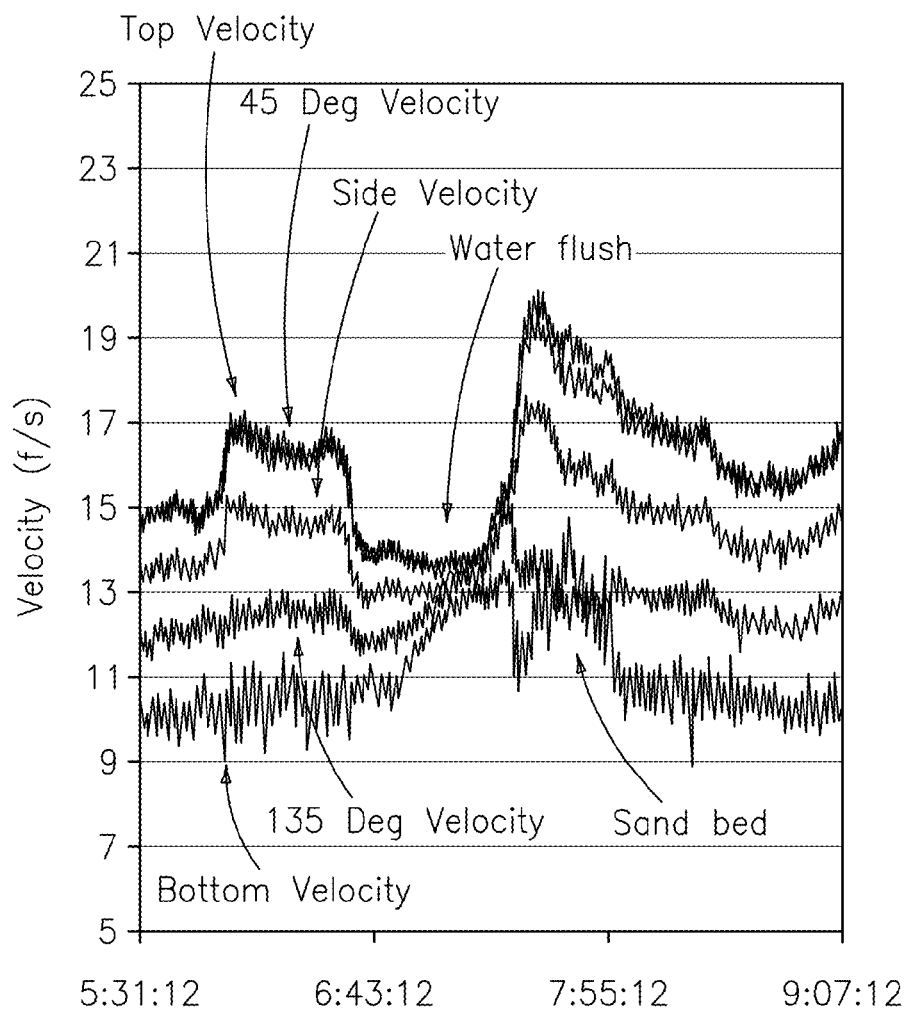
FIG. 14: Detection of water flush (no stratification) and sand bed deposition in slurry pipeline in the field

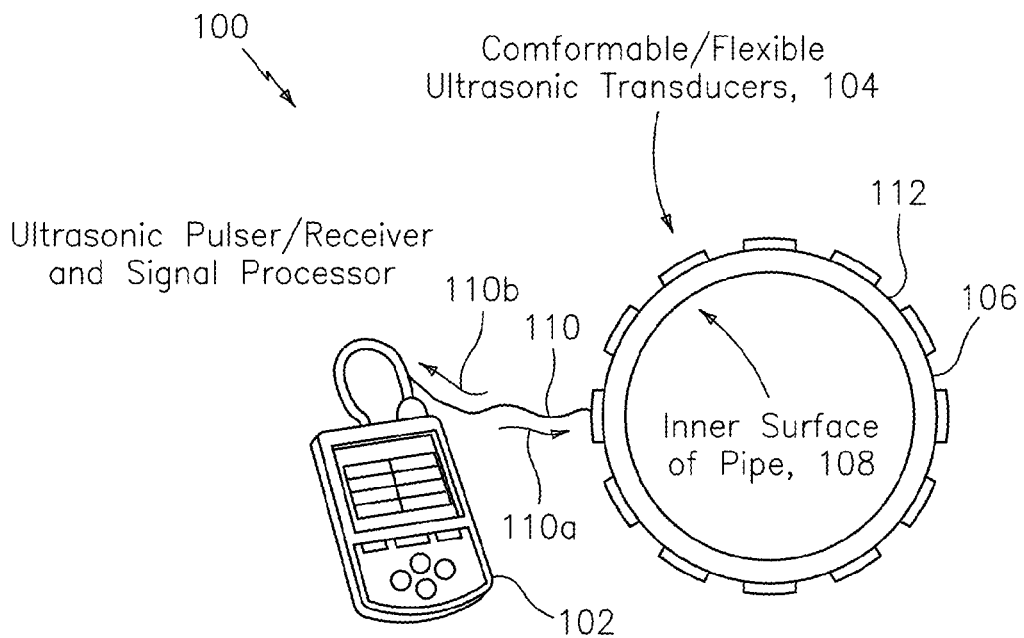
FIG. 15b
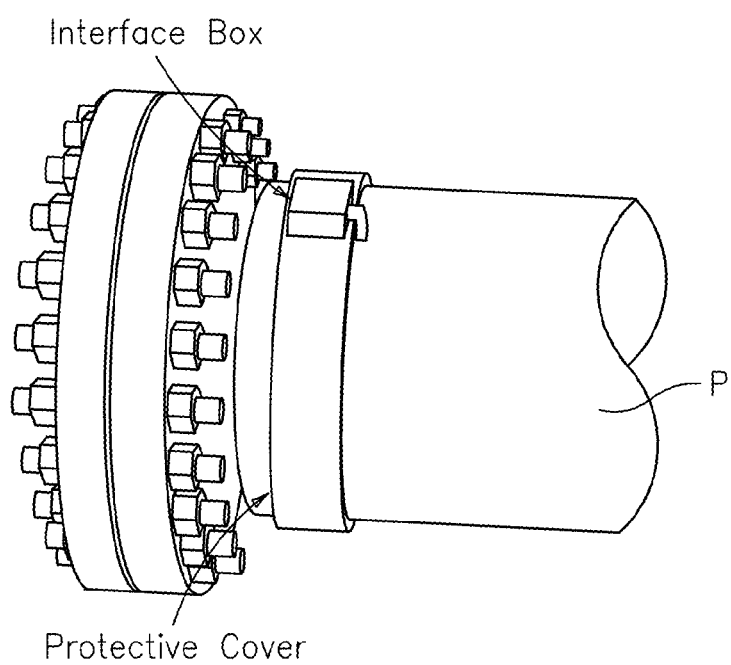
FIG. 15a: Conceptual layout of system and picture of system in operation at site Ultrasonic Pulser/Receiver and signal Processor 102 one or more modules 102a configured to respond to a signal containing information about a wave propagated through a wall of a pipe and to provide a corresponding signal containing information about a determination related to a thickness of the wall of the pipe Other modules 102b

*FIG. 15c*

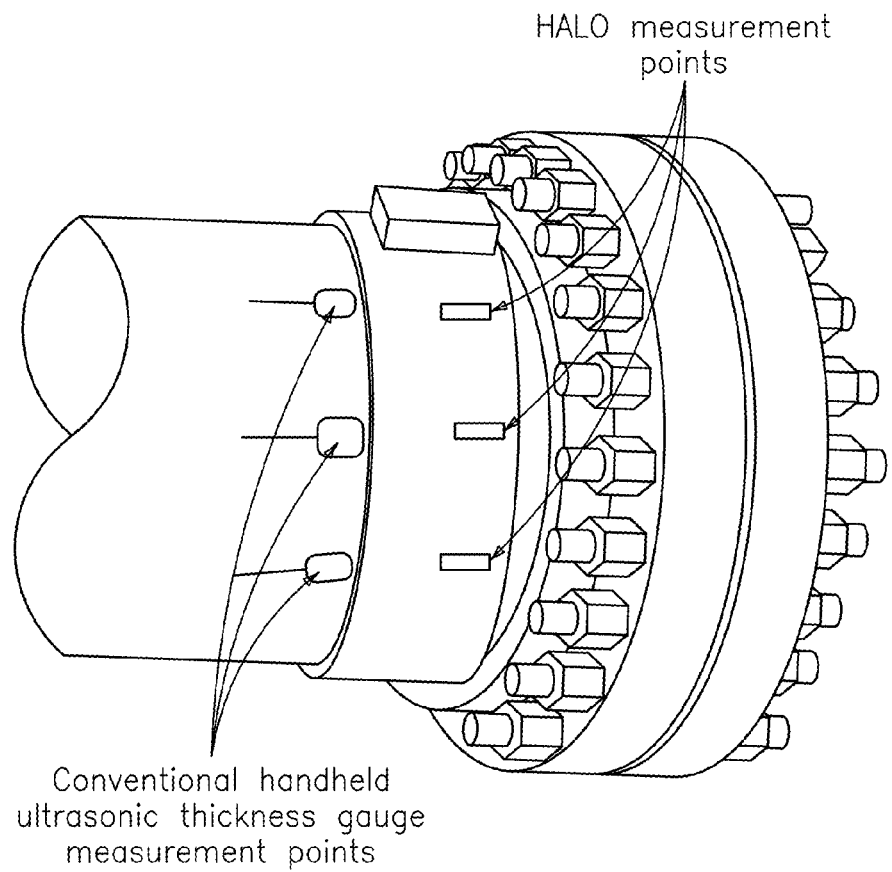
FIG. 16: Pipe wall thickness measurement points to compare conventional technique with invention

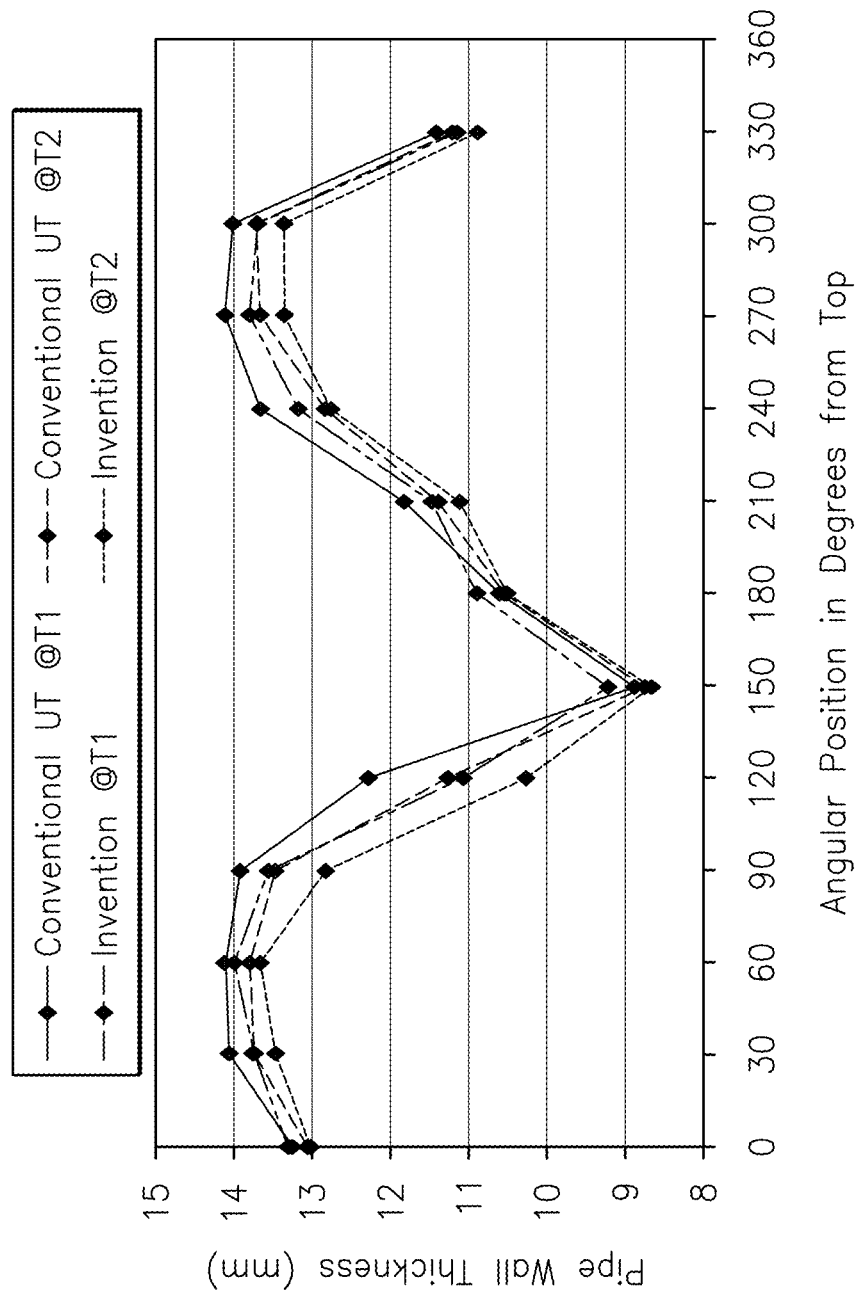
FIG. 17: Conventional ultrasonic (UT) pipe wall thickness measurement versus HALO™ measurements

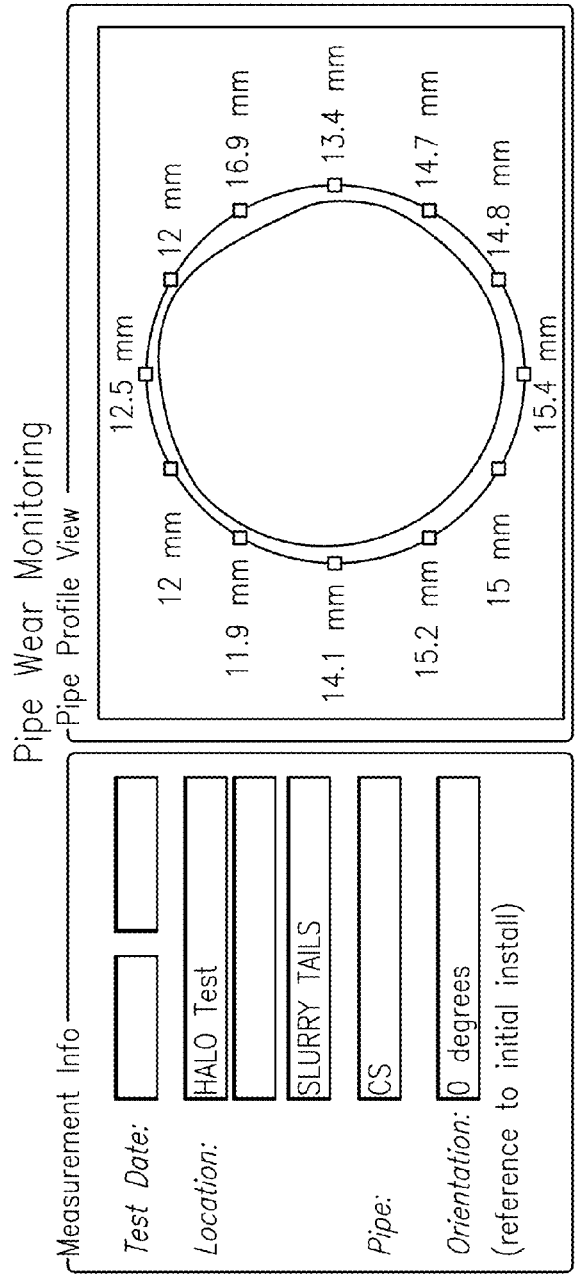
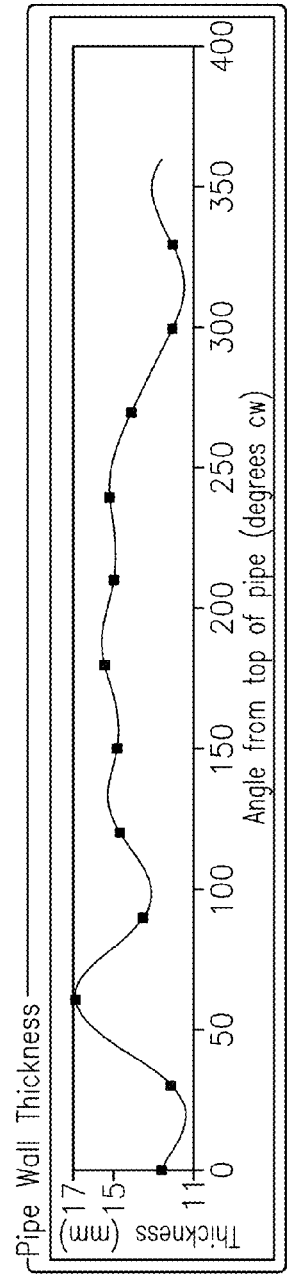
FIG. 18: Pipe wall thickness visualization software output

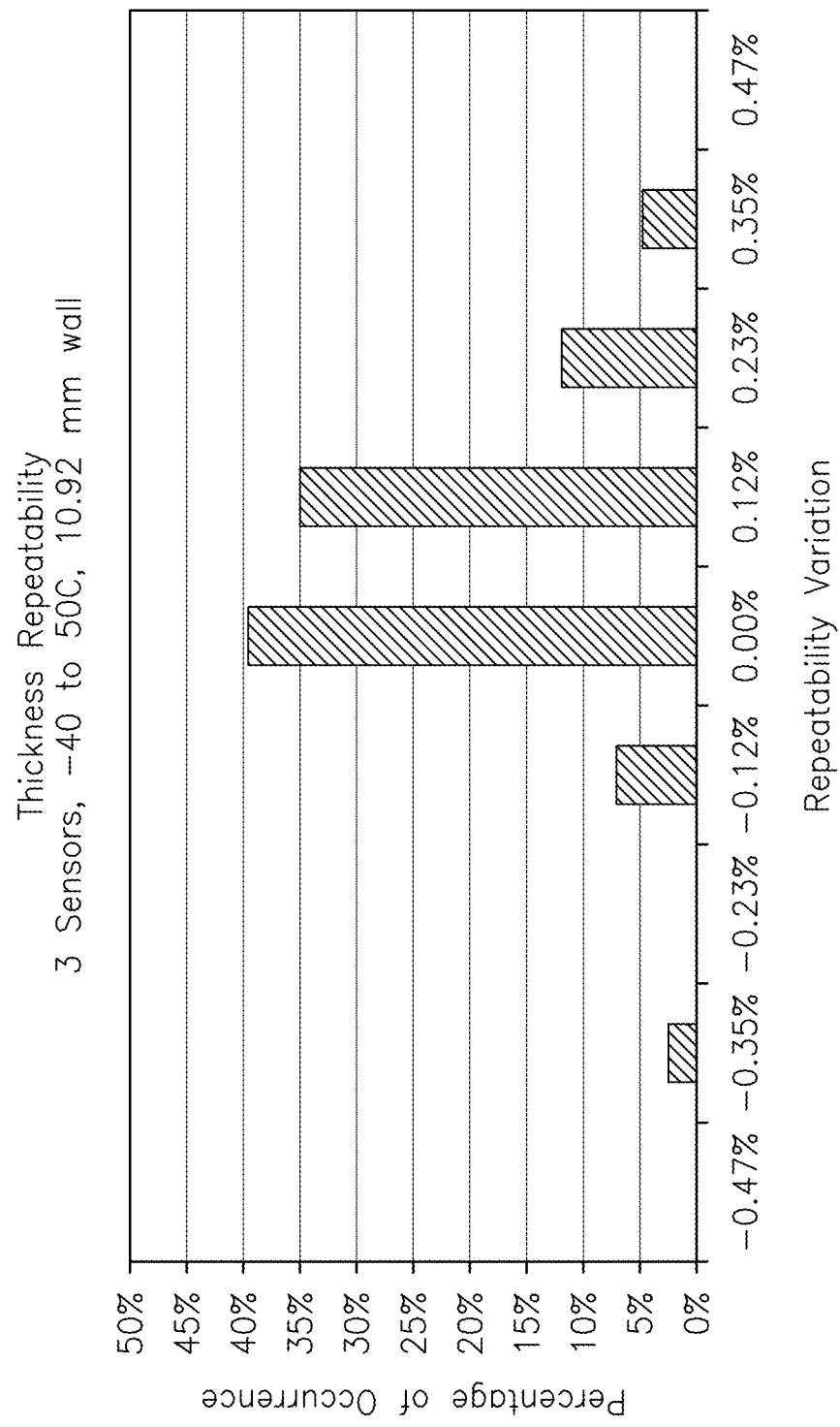
FIG. 19: Small spread in data over 90C temperature range and over three sensors is shown

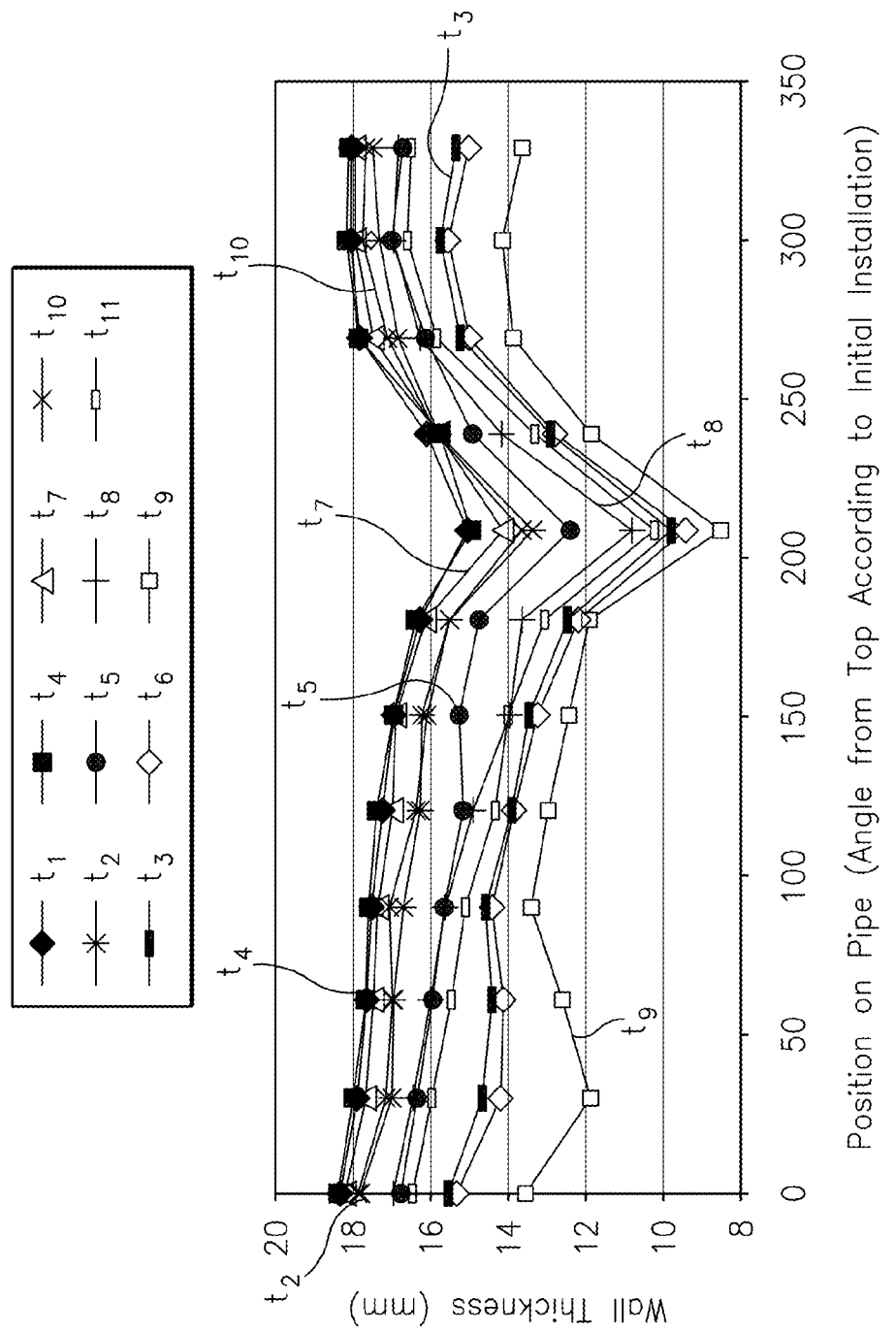
FIG. 20: Measurement of pipe wall thickness as a function of angular position and time is shown FIG. 21: Inner surface irregularities seen on chromium-steel worn pipe

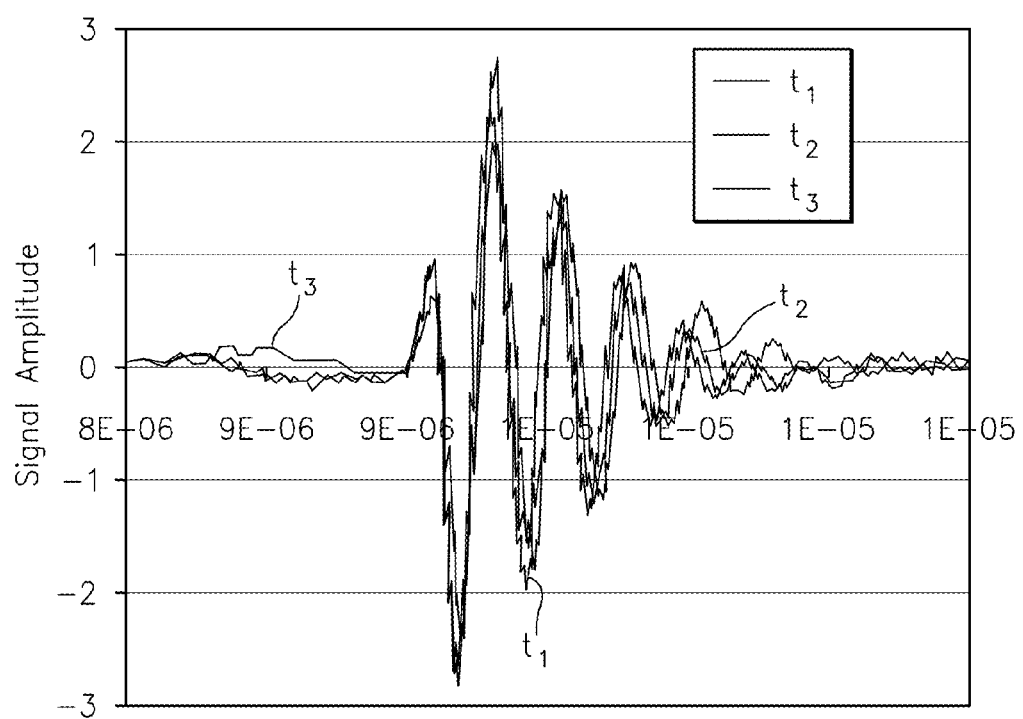
FIG. 23: Long Term High Temperature Testing

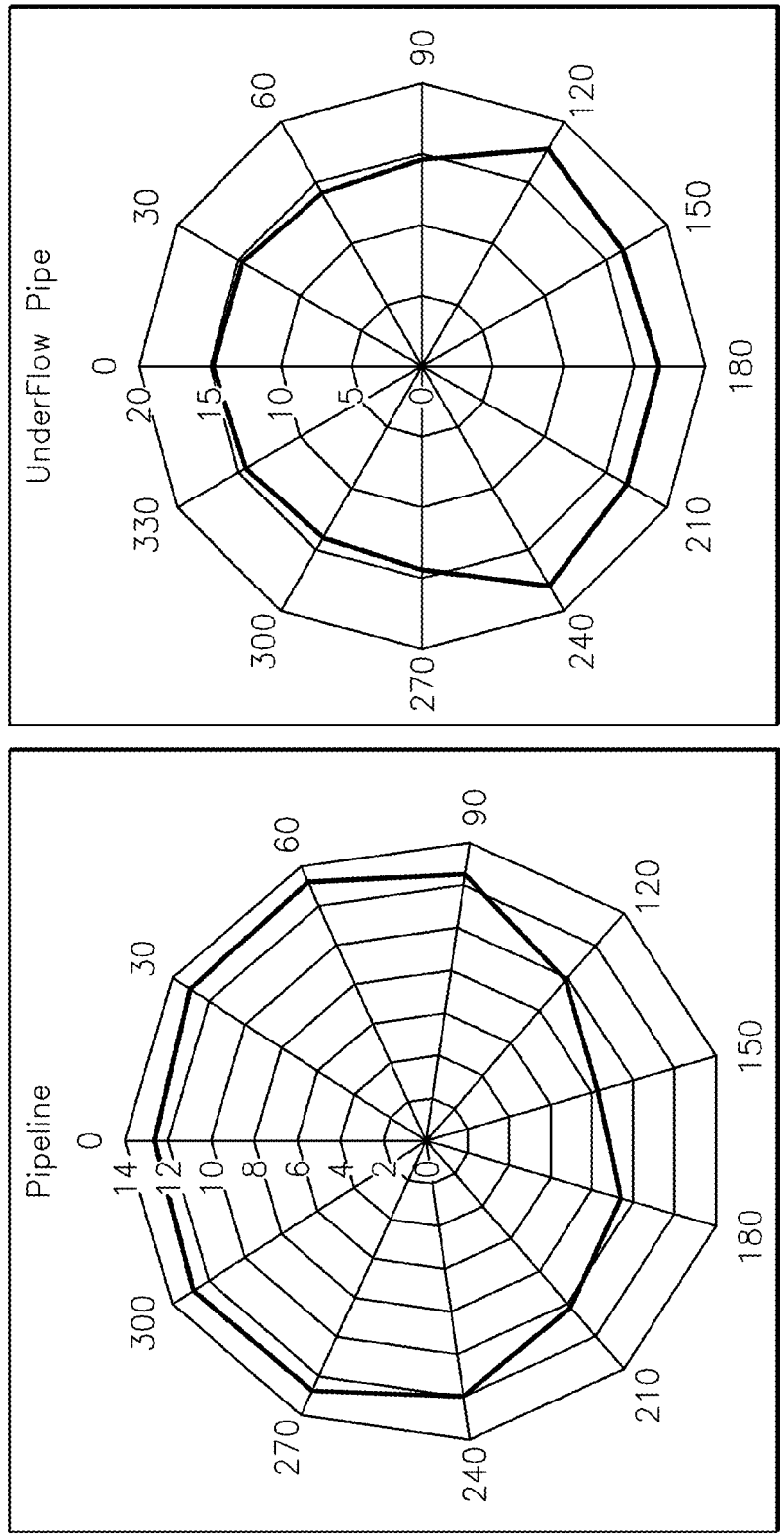
FIG. 29: Pipe wall thickness in millimeters as a function of angular position from top of pipe as shown on two different pipes

WEAR MONITORING WITH ROTATIONAL SENSOR AND SENSOR THICKNESS

CROSS-REFERENCE TO RELATED APPLICATIONS

This is a continuation application that claims benefit to patent application Ser. No. 12/922,261, file 30 Nov. 2010, which is hereby incorporated by reference in its entirety, which claims benefit to international patent application serial no. PCT/2009/037269 filed 16 Mar. 2009 benefit to provisional patent application Ser. No. 61/133,878, filed Jul. 2, 2008; Ser. No. 61/103,686, filed Oct. 8, 2008; Ser. No. 61/117,762, filed Nov. 25, 2008; Ser. No. 61/036,689, filed Mar. 14, 2008; and Ser. No. 61/054,612, filed May 20, 2008, which are all also incorporated by reference in their entirety.

BACKGROUND OF THE INVENTION

1. Field of Invention

This invention relates to a technique for non-invasive and real-time measurement of a velocity profile of a media flowing in a pipe.

This invention also relates to a technique for measurement and trending of pipe wear of media flowing in a pipe.

More particularly, this invention also related to using these techniques in relation to media such as a slurry.

2. Description of Related Art

Historically, flow measurements in the mineral processing industry have suffered from the limitations of previously available flow meter technology including commonly used instruments such as ultrasonic meters, electromagnetic meters, turbine meters, orifice plate meters, vortex flow meters, Coriolis meters, and Venturi meters. Sonar array flow measurement technology, which entered the mineral processing industry about four years ago, has overcome many of these limitations. The development of this technology began about ten years ago with the specific goal of non-invasively measuring multi-phase flows in the petroleum industry. The same technology was later adapted to the mineral processing industry where it has experienced rapid adoption.

By way of example, there has been a long history of using ultrasonics based nondestructive testing to determine the wall thickness of metallic pipes. To date this method of determining wall thicknesses has been costly, unreliable, and of limited use for trending wear rates.

In view of this, there is a need in the industry to reduce the high labor costs associated with this method and to decrease the variance found in these manually performed measurements.

SUMMARY OF THE INVENTION

The present invention provides new techniques for non-invasive and real-time measurement of the velocity profile of slurry flow in horizontal pipes. This information can be used to determine the approach and onset of solid deposition on the bottom of the pipe. Having this information in real time can enable operation at lower velocities or higher solids concentration or both while avoiding solids deposition or plugging and their associated operational costs.

In addition, the present invention provides new techniques advances in the measurement and trending of pipe wear on slurry lines. In contrast to known manual methods, the present invention uses a permanently or semi-permanently installed ring of conformable ultrasonic transducers clamped onto the outside of the pipe. These transducers are used to measure the thickness of the pipe under their respective locations. This results in better repeatability, accuracy, and failure prediction, along with reduced labor costs. The benefit is significantly improved pipe wear monitoring in pipelines with abrasive solids. This provides an improvement in the ability to insure safe operation and avoidance of costly operational and environmental damage due to leaks caused by pipe wear.

The specific sensor technology, based on piezoelectric film sensors, provides unique measurement capabilities. The first of these is the ability to non-invasively measure localized strains in the walls of pipes. Combined with sonar array processing algorithms, an axial array of such sensors can measure flow velocities within a pipe. Using this principle, sets of these axial sensor arrays arranged at different circumferential locations of a pipe can measure several fluid velocities at various heights in the pipe, thus providing a real-time velocity profile.

A second application of this piezoelectric sensor technology once again uses a circumferential array of permanently mounted piezoelectric film sensors but without the axial array components. Through active excitation of the piezoelectric film sensors, multiple measurements of pipe wall thickness at a single axial location can be obtained, thus providing a highly accurate and repeatable means of monitoring pipe wear due to abrasive slurry flow.

Pipe Wall Thickness Measurement

In applications related to pipe wall thickness measurements, the present invention may take the form of apparatus featuring one or more modules configured to respond to signaling containing information about a wave propagated through a wall of a pipe and to provide a corresponding signal containing information about a determination related to a thickness of the wall of the pipe. In this case, the apparatus is a signal processor that processes signaling received from a transducer module mounted on the wall of the pipe.

According to some embodiments of the present invention, the one or more modules may be configured to make the determination based at least partly on an amount of time the wave propagates through the wall of the pipe, including the time a traveling stress wave travels to and is reflected back from an inner wall of the pipe.

According to some embodiments of the present invention, the apparatus may further include a transducer module mounted on the wall of the pipe, including an ultrasonic transducer module, configured separately or together with the signal processing apparatus described above.

According to some embodiments of the present invention, the one or more modules may be configured to provide an input signal to the transducer module, including an electrical input signal, and the transducer module may be configured to propagate the wave through the wall of the pipe.

According to some embodiments of the present invention, the transducer module may include a series, a ring or circumferential array of transducers that are permanently or semi-permanently mounted around a perimeter of the wall of the pipe. Each transducer may be configured to respond to an input signal from the one or more modules and provide the wave that is propagated through the wall of the pipe, and may also be configured to respond to the wave reflected off an inner surface of the wall of the pipe and returned back to said each transducer, and provide the signaling in the form of an output signal containing information about the same that can be used to determine the thickness of the wall of the pipe back to the one or more modules of, e.g., the signal processing apparatus described above.

According to some embodiments of the present invention, the one or more modules may be configured to determine the thickness of the wall of a steel pipe or a polymer pipe.

According to some embodiments of the present invention, the one or more modules may be configured to determine an absolute thickness of the wall of the pipe, or a relative thickness of the wall of the pipe, including a pipe wall thickness trend based on a comparison of the thickness of the wall of the pipe performed at two different periods of time.

According to some embodiments of the present invention, the one or more modules may be configured to provide the corresponding signal containing information about a graph to provide a visual indication of the thickness of the wall of the pipe. The graph may be a polar plot that provides the thickness of the wall of the pipe as a function of the angular distance from a set reference point of the pipe.

According to some embodiments of the present invention, the one or more modules may be configured to determine an interpolation of the thickness of the wall of the pipe between one or more pairs of sensor points in the series, ring or circumferential array of transducers.

According to some embodiments of the present invention, the transducer module may include a piezoelectric element, including one made of PVDF material, as well as other types of kind of material either now known or later developed in the future.

According to some embodiments of the present invention, the series, ring or circumferential array of transducers may be equally spaced circumferentially around the perimeter so as to provide a complete picture of the thickness of the wall of the pipe. The series, ring or circumferential array of transducers may include ultrasonic transducers, as well as other types of kind of sensors either now known or later developed in the future.

According to some embodiments of the present invention, the one or more modules may be configured to form part of either a portable device hand carried to the series, ring or circumferential array of transducers, or configured to be mounted near or next to the series, ring or circumferential array of transducers, e.g., at or one a customer site. The scope of the invention is not intended to be limited to the type or kind of device in which the one or more modules may be configured or implemented.

According to some embodiments of the present invention, the transducer module may be configured as an ultrasonic signal transmitter and receiver that receives an input signal from the one or more modules, and that provides the signaling containing information about the wave propagated through the wall of the pipe back to the one or more modules.

According to some embodiments of the present invention, the transducer module may be configured as a dual transducer, having one transducer configured to receive an input signal from the one or more modules, and having another transducer configured to provide the signaling containing information about the wave propagated through the wall of the pipe back to the one or more modules. The transducer module may also be configured in two parts, a first part being a transducer part, and a second part being an optional spacer. The transducer part may be configured to inject the wave or pulse into the optional spacer so as to travel to an inner wall part of the pipe, such that the wave or pulse hits an outer wall of the pipe and some amount thereof is reflected back along with a reflection of another amount from the inner wall part of the pipe at a certain time later, and where the difference between these two detected waves or pulses is proportional to the thickness of the wall of the pipe. The transducer part may be configured to inject the wave or pulse into the wall of the pipe that will continue to bounce back-and-forth producing a series, ring or circumferential array of equally spaced pulses, and where the thickness of the wall of the pipe is determined by the time between successive pulses being measured, so as to eliminate the requirement for absolute timing based on the injected pulse. The transducer part is configured to detect received pulses with any one or more signal processing techniques, including a simple peak detection, as well as a quadrature, homodyne or heterodyne demodulation.

According to some embodiments of the present invention, the one or more modules may be configured to determine a substantially continuous wall thickness prediction around the perimeter.

According to some embodiments of the present invention, the one or more modules may be configured to determine a future pipe condition prediction around the perimeter, including the future pipe condition prediction being based on the orientation of the pipe.

According to some embodiments of the present invention, the one or more modules may be configured to make the determination based on the orientation of the series, ring or circumferential array of transducers around the perimeter. The one or more modules may also be configured to make the determination based on the recordation of data related to the orientation of the series, ring or circumferential array of transducers around the perimeter.

According to some embodiments of the present invention, the apparatus may include a band configured and arranged to compress the series, ring or circumferential array of transducers against the wall of the pipe, including a metal band.

According to some embodiments of the present invention, the apparatus may include a compliant backing material, including rubber, configured and arranged between the band and the series or ring of transducers to cushion and allow the series, ring or circumferential array of transducers to conform to the shape of the wall of the pipe.

According to some embodiments of the present invention, one or more of the series, ring or circumferential array of transducers may be coupled to the wall of the pipe using a couplant taking the form of a solid gel, a liquid gel, or some combination thereof, so as to substantially eliminate air pockets and maximize a signal path between the series, ring or circumferential array of transducers and the wall of the pipe.

According to some embodiments of the present invention, the one or more modules may be configured to interpolate based on either cubic spline or polynomial regression techniques, or a Fourier decomposition technique, that are known curve fitting routines. When implementing the Fourier decomposition technique, the one or more modules may be configured to determine various Fourier components required to create a curve which includes all sample or sensor points and to determine intermediate locations between the sample or sensor points. The one or more modules may also be configured to use custom tailored weighting coefficients on Fourier components. The one or more modules may also be configured to limit the magnitude of one or more derived Fourier components to physically realistic value points so as to identify and discard a derived Fourier component from a data set.

According to some embodiments of the present invention, the one or more modules may be configured to determine the future pipe condition prediction using an extrapolation technique, including determining a calculated wear model or profile using some combination of, e.g., a least-square polynomial extrapolation and Fourier component extrapolation. The one or more modules may also be configured to determine a lifetime schedule or a rotation schedule for the pipe to substantially optimize the viable lifetime of the pipe, including when the pipe should be rotated and/or at which angle so as to distribute substantially equally the wear of the pipe around the inner wall of the pipe. The one or more modules may also be configured to determine trigger points that can be used to predict certain wall thickness configurations requiring intervention from maintenance personnel.

According to some embodiments of the present invention, the one or more modules may be configured to provide an input signal containing information about an adjustment to the frequency of the wave propagated through the wall of the pipe based at least partly on the signal-to-noise ratio of the signal.

According to some embodiments of the present invention, the apparatus comprises may include an ultrasonic signal pulser and receiver configured to adjust the frequency of the wave propagated through the wall of the pipe by modulating the phase of an ultrasonic signal with an m-sequence code. The ultrasonic signal pulser and receiver may be configured to correlate the m-sequence code with a known code and to detect a desired signal from system noise and other non-coherent reflections.

The present invention may also take the form of a method featuring steps of responding in one or more modules to signaling containing information about a wave propagated through a wall of a pipe; and providing a corresponding signal containing information about a determination related to a thickness of the wall of the pipe. The scope of the invention is also intended to include the method also having one or more steps related to the other features set forth above in relation to the description of the overall apparatus described herein.

The present invention may also take the form of a system featuring a series, a ring or circumferential array of transducers permanently or semi-permanently mounted around a perimeter of the wall of the pipe and a signal processor device, where the series, the ring or circumferential array of transducers is configured to provide the signaling containing information about a wave propagated through a wall of a pipe, and where the signal processor device is configured to respond to the signaling and provide a corresponding signal containing information about a determination related to a thickness of the wall of the pipe. The scope of the invention is also intended to include the system having one or more of the other features set forth above in relation to the apparatus described herein.

The present invention may also take the form of a computer-readable storage medium having computer-executable components for performing a method comprising: steps of responding in one or more modules to signaling containing information about a wave propagated through a wall of a pipe; and providing a corresponding signal containing information about a determination related to a thickness of the wall of the pipe. The scope of the invention is also intended to include the computer-readable storage medium having one or more steps related to the other features set forth above in relation to the description of the method and apparatus described herein.

One advantage of the present invention is that it has resulted in decreased labor costs, better measurement repeatability, and more timely pipe wear measurement results. It also has allowed pipe wall measurements to be performed where inspectors cannot safely and easily perform these measurements currently.

Velocity Profile Measurement

Further, in applications related to velocity profile measurements, the present invention may take the form of apparatus featuring one or more modules configured to respond to signaling containing information about coherent disturbances of a media flowing in a pipe and to provide a corresponding signal containing information about a measurement of a velocity profile of the media flowing in the pipe. In this case, the apparatus is a signal processor that processes signaling received from sensors mounted on the wall of the pipe.

According to some embodiments of the present invention, the coherent disturbances may include density variations, temperature variations, or turbulent eddies.

According to some embodiments of the present invention, the velocity profile may include several fluid velocities at various heights in the pipe.

According to some embodiments of the present invention, the apparatus may also feature an axial array of sensors configured to respond to the coherent disturbances of the media flowing in the pipe and to provide the signaling containing information about the coherent disturbances of the media flowing in the pipe. The axial array of sensors may be configured separately or together with the signal processing apparatus described above. The axial array of sensors may be configured to respond to localized strains on the inside of the pipe wall caused by the coherent disturbances and provides the signaling. The axial array of sensors may also be wrapped partially or fully around the pipe. The sensors may also be spaced a predetermined distance from each other along the axial direction of the pipe. The separate between the sensors in the axial array may be shorter than the length of coherent disturbances, thereby resulting in similar voltage signatures from each sensor in the array with only a delay in time.

According to some embodiments of the present invention, the one or more modules may be configured to apply a sonar array processing algorithm to output signals of the axial array of sensors and to determine the velocity at which coherent disturbances pass through the axial array of sensors.

According to some embodiments of the present invention, the apparatus may also feature multiple arrays of sensors located at different circumferential positions on a single band to measure the velocity profile of the media flowing in the pipe, where each array configured to respond to the coherent disturbances of the media flowing in the pipe and to provide the signaling containing information about the coherent disturbances of the media flowing in the pipe.

The present invention may also take the form of a method featuring steps of responding in one or more modules to signaling containing information about coherent disturbances of a media flowing in a pipe and providing a corresponding signal containing information about a measurement of a velocity profile of the media flowing in the pipe. The scope of the invention is also intended to include the method also having one or more steps related to the other features set forth above in relation to the description of the overall apparatus described herein.

The present invention may also take the form of a system featuring one or more transducers mounted around a perimeter of the wall of the pipe and a signal processor device, where the one or more transducers is configured to provide signaling containing information about coherent disturbances of a media flowing in a pipe, and where the signal processor device is configured to respond to the signaling and provide a corresponding signal containing information about a measurement of a velocity profile of the media flowing in the pipe. The scope of the invention is also intended to include the system having one or more of the other features set forth above in relation to the apparatus described herein.

The present invention may also take the form of a computer-readable storage medium having computer-executable components for performing a method comprising: steps of responding in one or more modules to signaling containing information about coherent disturbances of a media flowing in a pipe and providing a corresponding signal containing information about a measurement of a velocity profile of the media flowing in the pipe. The scope of the invention is also intended to include the computer-readable storage medium having one or more steps related to the other features set forth above in relation to the description of the method and apparatus described herein.

According to some embodiments of the present invention, the one or more modules is configured to determine the vertical distance over which the flow is averaged for each array based on the size of the array elements, the size of the pipe, and the circumferential location of each array on the pipe.

BRIEF DESCRIPTION OF THE DRAWING

The drawing includes FIGS. 1-33, which are not drawn to scale, as follows:

FIG. 1 is a cutaway of a pipe under a sonar array sensor band illustrating turbulent eddies.

FIG. 2 is an illustration of a signal detected by passive sensors in an array from one collection of turbulent eddies.

FIG. 3, including FIGS. 3a, 3b, 3c and 3d, shows various flows in a pipe, including homogeneous flow (FIG. 3a); heterogeneous flow with full suspended particles (FIG. 3b); heterogeneous flow with moving bed (FIG. 3c); and heterogeneous flow with stationary bed (FIG. 3d).

FIG. 4 is a diagram of a slurry test loop setup.

FIG. 5 is a graph of velocity (m/s) and density gauge (kg/m$^3$) versus time (hrs:min:sec) showing a velocity profile of an 89 micron mining slurry.

FIG. 6 is a graph of velocity (m/s), and alarm state and density gauge (kg/m$^3$), versus time (hrs:min:sec) showing an alarm state of an 89 micron mining slurry.

FIG. 7 includes two graphs, including FIG. 7a showing a graph of height (diameters) versus a normalized velocity for mostly homogeneous flow, suspended particles, and FIG. 7b showing a graph of height (diameters) versus a normalized velocity for mostly heterogeneous flow with suspended particles.

FIG. 8 showing a graph of height (diameters) versus a normalized velocity for a heterogeneous flow with a stationary solids bed.

FIG. 9 is a graph of flow velocity (m/s) and density (kg/m$^3$) versus time (hrs:min:sec) showing 186 micron slurry solid deposition detected by sonar meter, densitometer, and delta-pressure.

FIG. 10 is a graph of normalized height (diameter) in relation to flow (m/s) showing velocity profiles versus a reference velocity.

FIG. 11 is a graph of three-dimensional velocity profiles and velocity contours in an inhomogeneous flow.

FIG. 12, including

FIG. 13 is a graph of velocity (f/s) and sanding factor versus time (hrs:min:sec) showing the detection of a sand bed and development of a sand bed in a slurry pipeline in the field.

FIG. 14 is a graph of velocity (f/s) versus time (hrs:min:sec) showing the detection of water flush (no stratification) and a sand bed deposition in a slurry pipeline in the field.

FIG. 15a is an illustration of a system in operation at a site, and FIG. 15b is an illustration of a conceptual layout of a system; and FIG. 15c is a block diagram of an ultrasonic pulser/receiver and signal processor according to the present invention.

FIG. 16 is an illustration of a comparison of pipe wall thickness measurement points according to the present invention and a conventional technique.

FIG. 17 is a graph of pipe wall thickness (mm) versus an angular position (degrees) from the top showing a conventional ultrasonic pipe wall thickness measurement versus a measurement according to the present invention.

FIG. 18 includes FIG. 18a which is a graph of pipe wall thickness (mm) versus an angular position (degrees) from the top showing a measurement according to the present invention, and FIG. 18b which is a view of a pipe profile with the data in FIG. 18a.

FIG. 19 is a graph of percentage of occurrence (%) versus a repeatability variation (%) showing a small spread in data over 90 C temperature range and over three sensors.

FIG. 20 is a graph of wall thickness (mm) versus position on pipe (angle from the top according to initial installation) showing a measurement of the pipe wall thickness as a function of angular position and time.

FIG. 21, including

FIG. 23 is a graph of signal amplitude versus time showing long term high temperature testing, having signal amplitude graphs for times $t_1$, $t_2$, $t_3$, where time $t_2$ is about one month after time $t_1$, and where time $t_3$ is about three months after time $t_1$.

FIG. 25, including

FIG. 27, including

FIG. 28, including

FIG. 29, including FIGS. 29a and 29b, includes graphs in polar coordinates of a pipeline and an underflow pipe showing pipe wall thickness (mm) as a function of angular position from the top of the pipe on two different pipes.

FIG. 30 shows measurements of 12 points around a wall of a pipe that can be used to interpolate measurement data at points in-between.

DETAILED DESCRIPTION OF BEST MODE OF THE INVENTION

I. FIGS. 1-14

Non-Invasive Velocity Profile Measurement

Figure 12A:
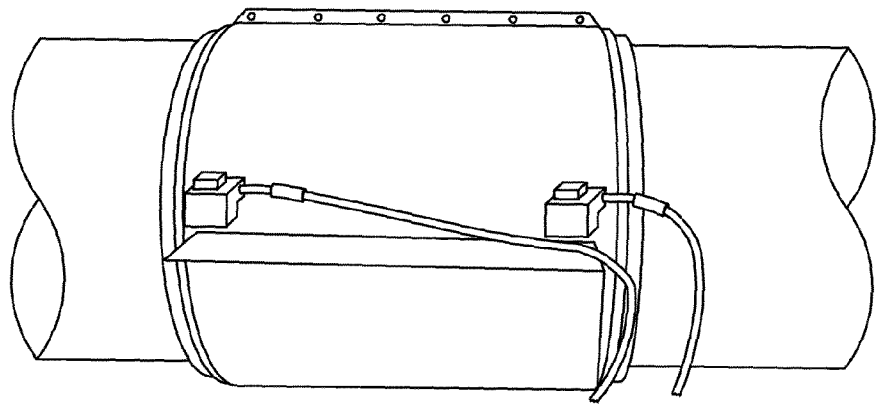
FIGS. 12a and 12b, is an illustration of a velocity profile monitoring system in operation at a site.

Principle of Operation for Passive Array Based Flow Measurement Using Sonar Processing Algorithms Sonar array-based meters track and measure the mean velocities of coherent disturbances traveling in the axial direction of a pipe. These disturbances can take many different forms and can propagate at different velocities. Their propagation method and velocities include convection with the flow (slowest velocity—fluid flow), propagation in the fluid or slurry (mid-range velocity—acoustics), and propagation in the pipe walls (fast velocity—vibrations). The sonar array-based meters discriminate between the three main propagation modes through a combination of frequency and velocity differences.

First, the description focuses on the disturbances that convect with the flow. These disturbances can be density variations, temperature variations, turbulent eddies, or others. Within most industrial processes, the most common flow disturbance is turbulence. Turbulent eddies, or vortices, are naturally present in flow regimes where Reynolds numbers are greater than 4000. The Reynolds number represent the ratio of inertial forces to viscous forces and numbers greater than 4000 are said to be turbulent and less than 2300 are considered to be laminar. The larger the Reynolds number, the broader the range of turbulent eddies within the flow. The fundamental principle of sonar flow measurement is based on tracking these turbulent eddies as they pass through an array of sensors (Gysling, D. and Mueller, E., (2004). Application of Sonar-Based Clamp-On Flow Measurement in Oils and Processing. *ISA* 2004 *Exhibit and Conference*). A cutaway illustration of these turbulent eddies within a pipe under a sonar array sensor band is shown in FIG. 1.

Through the combination of an array of passive sensors and the sonar array processing algorithms, the average axial velocities of a collection of vortices is obtained. The sequence of events that occur to make this measurement possible is as follows:

- As these turbulent eddies pass by any fixed location on the pipe, they will exert a small dynamic stress on the inside of the pipe wall
- The strain induced in the pipe wall from these dynamic stress fluctuations is converted to an electrical signal through a passive sensor wrapped partially or fully around the pipe (FIG. 2 exaggerates)—no couplant gels or liquids are required since these are low frequency mechanical strains and not ultrasonics
- The unique electrical signal from each collection of turbulent eddies is detected by each element of the array of sensors. These sensors are spaced a precisely set distance from each other along the axial direction of the pipe.
- The separation between sensors in the array is shorter than the coherence length of the turbulent eddies, thereby resulting in similar voltage signatures from each sensor in the array with only a delay in time.

When sonar array processing is applied to the output signals of the array, the velocity at which these turbulent eddies pass through the array of sensors is determined, thus providing the propagation speed of the fluid within the pipe (Nelson, R. O., (2001). Sonar Signal Processing, Artech House Inc., Norwood, Mass., USA, ISBN 0-89006-453-9).

This process is illustrated with one collection of turbulent eddies in FIG. 2, but in practice is applied to numerous collections of turbulent eddies. In FIG. 2, the apparatus or system, generally indicated as 10, features a sensor array 12 arranged in relation to a pipe 14; amplifiers and digitizers 16 that receive sensor array signaling containing information about coherent disturbances 14*a* of a media flowing in the pipe 14, and amplifier and digitizer the sensor array signaling; and one or more modules 18 configured to respond to signaling containing information about coherent disturbances 14*a* and to provide a corresponding signal along line 18*a* containing information about a measurement of a velocity profile of the media flowing in the pipe.

By way of example, and consistent with that described herein, the functionality of the one or more modules 18 may be implemented using hardware, software, firmware, or a combination thereof, although the scope of the invention is not intended to be limited to any particular embodiment thereof. In a typical software implementation, the one or more modules 18 would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology now known or later developed in the future. Moreover, the scope of the invention is intended to include the one or more modules 18 being a stand alone module, as shown, or in the combination with other circuitry for implementing another module. Moreover, the real-time part may be implemented in hardware, while non real-time part may be done in software.

Velocity Profile in Horizontal Pipelines

In mining and oil sands applications a vast majority of product and tailings transport is done as slurry. Flow regimes of horizontal flows can be classified into four distinct groups: homogeneous flow with fully suspended particles, heterogeneous flow with all particles suspended, flow with a moving bed, and flow with a stationary bed. (See Cheremisinoff, N. P., (1986). Encyclopedia of Fluid Mechanics. Vol. 5, Slurry Flow Technology, Golf Pub. Co.) The flow regime is dependent upon properties of the slurry such as particle size, density, flow velocity, viscosity, and particle size distribution, as well as the physical attributes of the pipeline such as diameter and surface roughness. FIG. 3 shows the particle distribution for each of these regimes.

In fully developed homogeneous liquid flows, the profile is symmetric about the pipe axis, and does not pose the danger of developing a sand bed which can potentially lead to plugging of the pipeline. In this type of flow, the profile has a radial position dependency. Few slurry flows will be purely homogeneous flows. Most slurry flows will fall into the category of heterogeneous flow with some containing the characteristics of both homogeneous and heterogeneous flow. In heterogeneous flows, there is a stratification of the solids with a higher concentration of solids at the bottom of the pipe. For the same particle size, density, viscosity, particle size distribution and physical attributes of the pipeline, the flow velocity will determine the type of heterogeneous flow, that is whether or not a sand bed has developed and the characteristics of the sand bed. In heterogeneous liquid flows, the profile is not symmetric about the pipe axis. Instead, it is symmetric about the horizontal axis but asymmetric about the vertical axis due to the vertical distribution of particles.

Sonar Array Velocity Profiling Meter

The standard clamp-on flow meter is based on using a single multiple element array which provides for a measurement of the average flow velocity in a pipe. This clamp-on technology has been extended by implementing multiple arrays located at different circumferential positions on a single band, to measure the velocity profile of the fluid. This new tool offers process operators a non-invasive measurement tool with the ability to monitor and control the profile of their process flow. The following sections summarize the results of flow loop testing and field testing performed on a sonar array profiling system and demonstrates some of the potential benefits, one of which is the ability to detect the onset of sand-out conditions. Early detection of this condition allows operators the time to apply corrective actions and avoid catastrophic process shutdown. In addition, monitoring the profile can provide useful information about the properties of the process fluid which can allow operators to adjust production variables to optimize the process.

The velocity profile meter uses arrays located circumferentially on the outside of the pipe at the top, 45 degrees from the top, on the side, 135 degrees from the top and at the bottom of the pipe. The circumferential location of the sensor arrays is shown in FIG. 5. The size of the array elements, the size of the pipe, and the circumferential location of each array on the pipe determines the vertical distance over which the flow is averaged for each array. Testing of this technology has been accomplished at several customer sites and at research facilities.

SRC Flow Loop and Test

One series of tests were conducted in a slurry test loop, shown in FIG. 4, at the Pipe Flow Technology Center of the Saskatchewan Research Council (SRC) in Canada. The scope of this test was to test slurries representative of different processes and different stages in a process. For the first slurry test an 89 m d50 particle size was selected with a mixture density of 1300 kg/m³. The second slurry test started out with a m particles. Clay and larger stones were coarser sand slurry containing 186 added subsequently to the mixture. A velocity step down test was run for each slurry type to measure the velocity profile as a function of velocity.

Slurry Test Results

89 Micron Slurry

The results of the 89 micron slurry test are graphed in FIG. 5. The velocity was stepped down in the following increments to develop a sand bed—4 m/s, 3 m/sec, 2 m/s, 1.75 m/s 1.5 m/s, 1.4 m/s, 1.3 m/s, 1.2 m/s, 1.1 m/s, 1.0 m/sec, 0.9 m/s, 0.8 m/s, and 0.7 m/s. The flow was held at each flow rate for a period of 5 minutes to allow the loop to stabilize. Continuous flow data was recorded during the entire testing time. FIG. 5 shows the step down in flow rate and the corresponding velocities measured at each of the five sensor array positions. Also shown is the output of a densitometer positioned near the bottom (y/D=0.05) of the pipe to measure solids that stratify to the bottom. To obtain a reference flow velocity, a separate flow meter was installed in an 8" loop section where the higher flow velocity prevented solid deposition. This flow rate was then converted to an "equivalent 10 inch" velocity and graphed with the velocity profile data shown in FIG. 5.

As the flow rate is lowered the velocity profile changes to reflect the stratification changes within the pipe. It can be seen that as the flow rate decreases, the densitometer reading increases only slightly until approximately 1.5 m/s. At this velocity the density reading undergoes a step change reflecting an increase of solids at the bottom of the pipe.

Good agreement can be seen between the rapid increase in the Gamma Densitometer reading (set to measure density across the bottom of the pipe) and the relative velocities of the lower two sensors. Both indicate the formation of a bed at the same time. When the flow rate drops below the deposition velocity a bed starts to form on the bottom of the pipe and the Gamma Densitometer detects this rapid increase in density. The bottom sensor in the profile meter typically reads a lower velocity than the 135 degree sensor, due to the stratification of the slurry resulting in denser and slower moving layers near the bottom. When the bottom bed stops moving the bottom sensor detects signals from higher up in the pipe where the velocity is faster. This condition can cause the reported velocities of the bottom and 135 degree sensors to become more similar. FIG. 6 shows alarm conditions that can be generated based on the velocity differences measured by the different sensor bands. In FIGS. 7 and 8, measured velocity profiles are shown at three different flow velocities each showing three distinct flow regimes: mostly homogenous with all particles suspended (Left FIG. 7a), heterogeneous flow with all particles suspended (Right FIG. 7b) and heterogeneous flow with a stationary bed (FIG. 8). In the latter, the characteristic signal seen from a sand bed deposition is detected and the velocity calculated for pipe heights at the bottom and near the bottom of the pipe is set to zero.

Slurry Test Results

186 Slurry

For comparison with the previously discussed 89 micron slurry, FIG. 9 shows a step down test with the 186 micron d50 particle sized slurry. Once again, as the flow rate is lowered the velocity profile changes to reflect the stratification changes within the pipe. It can be seen that as the flow rate decreases the densitometer reading remains relatively constant at about 1600-1700 kg/m³, until at approximately 2.4 m/s it suddenly undergoes a step change reflecting an increase of solids at the bottom of the pipe. Additionally, FIG. 9 shows the pressure drop measured across the velocity profile meter, which in this case shows a sudden increase that coincides with the densitometer increase and the velocity overlaps of the bottom and 135° arrays of the velocity profile meter. Therefore the formation of the stationary solids bed was detected by the sonar velocity meter and confirmed by both the density and differential pressure measurements.

The velocity profile versus reference flow velocity is shown in FIG. 10. This plot shows that as the flow rate is reduced, two distinct changes occur to the profile. The first change is the velocity detected at the bottom of the pipe, which is the lowest velocity due to the high solids concentration. This velocity is slower relative to the velocity at the center of the pipe. Likewise, the velocities measured in the upper section of the pipe begin to move faster relative to the center of the pipe. The second change is that as the velocity is decreased further, solids are deposited on the bottom of the pipe as seen in the 1.9 m/s and 2.0 m/s flow rates.

FIG. 11 is a representation of the flow derived from the velocity profile data when coupled with flow profile models.

The resulting velocity calculations in the horizontal and vertical orientations can be visualized in a three-dimensional format and through contours.

Field Implementation

Figure 12B:
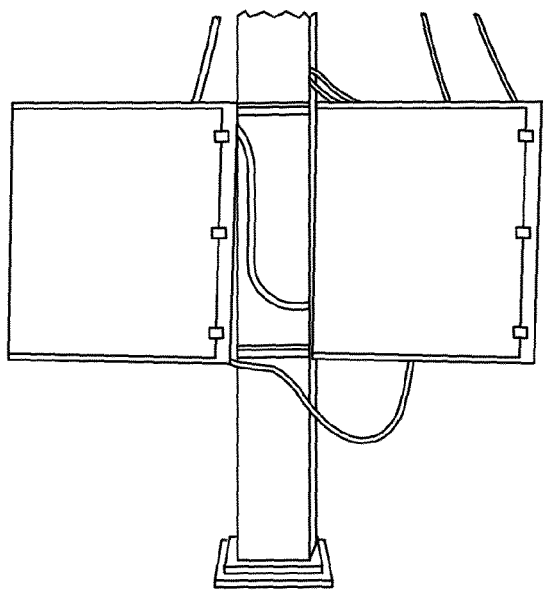

A field system has been monitoring velocity profile in a slurry solution with a wide range of particle sizes. This system directly reports the flow profile and sanding condition. A picture of this system in the field is shown in FIG. 12. The multiple sensor arrays are incorporated into a single band that is placed under the cover seen in the figure. This system monitors and logs the velocity at the previously discussed circumferential positions, which can be processed to determine the conditions leading to a potential sand bed development condition. In FIG. 13, velocity and alarm states from this field system are shown. The degree of stratification and other indications are used to determine when a sand bed has developed and when a sand bed is likely to develop. The slurry being monitored has a wide distribution of sizes and as a result a high level of stratification is expected even at the relatively high flow rates experienced by this pipeline. In FIG. 14, three states can be seen, heterogeneous flow, homogenous flow during a water flush and heterogeneous flow with a sand bed.

II. FIGS. 15-33

Pipe Wall Thickness Monitoring

FIGS. 15-33 show a new technique for non-invasive pipe wall thickness monitoring. FIG. 15a shows a conceptual layout of the apparatus or system a showing a pipe P, an interface box and a protective cover; while FIG. 15b shows the apparatus or system according to the present invention generally indicated as 100 that features an ultrasonic pulser/receiver and signal processor 102 and conformable/flexible ultrasonic transducers generally indicated as 104 arranged in relation to a pipe 106 having an inner surface 108.

FIG. 15c shows a block diagram of the ultrasonic pulser/receiver and signal processor 102 having one or more modules 102a and other modules 102b. In operation, the one or more modules 102a is configured to receive or respond to a signal or signaling 110b containing information about a wave propagated through a wall 112 of the pipe 106 and to provide a corresponding signal containing information about a determination related to a thickness of the wall 112 of the pipe 106. In this case, the apparatus takes the form of a signal processor that receives or responds to the signal or signaling 110b containing information about the wave propagated through the wall 112 of the pipe 106 from, e.g., the conformable/flexible ultrasonic transducers 104.

The corresponding signal may be provided to, e.g., to the other modules 102b, although the scope of the invention is not intended to be limited to where or to what device the corresponding signal is provided. For example, the corresponding signal may be provided to some other modules 102b for providing a visual indication of, e.g., either data or a graph of the thickness of the wall of the pipe. The corresponding signal may also be provided to some other circuit, module or signal processor either now known or later developed in the future, e.g. including some circuit, module or signal processor at some remote location.

In operation, the one or more modules is also configured to provide or pulse an input signal 110a to the transducers 104, which may include an electrical input signal. However, the scope of the invention is not intended to be limited to the transducers 104 itself providing or pulsing the input signal 110a. Embodiments are envisioned in which another device provides or pulses this input signal 110a.

The ultrasonic pulser/receiver and signal processor 102 may take the form of a handheld unit, or may take the form of a unit attached in the physical location of the transducers 104. Embodiments are also envisioned in which the ultrasonic pulser/receiver and signal processor 102 is arranged at a remote location and receives signaling from the transducers via a hardwire connection, a wireless interface or some combination thereof. The scope of the invention is not intended to be limited to where the ultrasonic pulser/receiver and signal processor 102 is located, or how the signaling is exchanged between the transducers 104.

By way of example, and consistent with that described herein, the functionality of the one or more modules 102a may be implemented using hardware, software, firmware, or a combination thereof, although the scope of the invention is not intended to be limited to any particular embodiment thereof. In a typical software implementation, the one or more modules 102a would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality described herein without undue experimentation. The scope of the invention is not intended to be limited to any particular implementation using technology now known or later developed in the future. Moreover, the scope of the invention is intended to include the one or more modules 18 being a stand alone module, as shown, or in the combination with other circuitry for implementing another module. Moreover, the real-time part may be implemented in hardware, while non real-time part may be done in software.

The other modules 102b may also include other modules, circuits, devices that do not necessarily form part of the underlying invention per se, e.g. including a pulsing circuit. The functionality of the other modules, circuits, device that do not form part of the underlying invention are known in the art and are not described in detail herein.

Principle of Operation for Pipe Wall Thickness Monitoring

The new pipe wear monitoring system according to the present invention uses a series of conformable ultrasonic transducers that are permanently or semi-permanently mounted around the perimeter of a pipe. These transducers are coupled to an ultrasonic pulser/receiver that sends an electrical signal to the ultrasonic transducer. The ultrasonic transducers convert the electrical signal into a traveling stress wave (ultrasonic wave) that propagates through the pipe wall, reflects from the inner surface of the pipe and returns to the ultrasonic transducer. The ultrasonic transducer then reconverts this returning stress wave into an electrical signal that is amplified and processed by the ultrasonic pulser/receiver. The ultrasonic pulser/receiver then determines the amount of time that it has taken the stress wave to travel from the transducer to the inner surface of the pipe and back to the transducer. Using the well known velocity for these stress waves in the pipe wall material, the thickness of the pipe wall can be accurately determined. This system is designed to measure the thickness of steel walled pipes but can be possibly extended to polymer pipes, depending on the wall thickness and material acoustic properties.

Comparison to Conventional Ultrasonic Thickness Measurement Instrumentation and Techniques The current or known baseline pipe wall thickness measurement technique consists of a handheld ultrasonic transducer and a portable pulser/receiver. One comparison between the system according to the present invention and a sophisticated handheld ultrasonic pipe wall thickness measurement tool revealed similar results. Measurements taken at the exact same points were not possible since the system according to the present invention was installed before the conventional ultrasonic measurements could be performed. The location difference may be in the axial direction but the circumferential locations were kept the same as shown in FIG. 16.

Small variations between the conventional ultrasonic technique and the system according to the present invention are due to the differences in axial location. The comparison was performed at two different periods of time to ascertain the ability to measure pipe wall thickness trends. The results shown in FIG. 17 reveal that there are some differences in the absolute wall thickness measured but more importantly that there are differences in the trends recorded between the two instruments. The system according to the present invention measured a reduction in wall thickness at all points, which was expected. In contrast, the conventional ultrasonic approach indicated that some measurement points showed no or minimal wear.

Measurement and Visualization of Pipe Wear

The pipe wall thickness measurements can be graphed in a polar plot to provide a visual indication of the wall thickness as a function of the angular distance from a set reference point on the pipe. New software that interpolates between sensor points and provides robustness in the possibility of erroneous data or a failed sensor has been implemented. The hardware, analysis and data management takes into account pipe rotations to monitor wear trends and project to the point in time at which the pipe wall safety margins have been crossed. An example of the visualization of the pipe wall thickness around the pipe is shown in FIG. 18. See also FIG. 29. In the plots, one can see thinner pipe walls at various angular locations around the pipe due to intentional rotations of the pipe performed to increase the pipe lifetime. In other situations, uneven pipe wear will result from changes in the flow profile after elbows or other pipe geometry effects.

Short Term Temperature Effects and Repeatability

This system has undergone testing for repeatability, impact of environmental temperature changes, and the impact of transducer to transducer variability. The results from varying these three factors may be consolidated into a single data set as shown in FIG. 19. An examination of the graph reveals that over 81% of the data is within +/−0.12% or +/−0.013 mm, and all the results are within +/−0.47% or +/−0.05 mm. The repeatability is well within the requirements to determine impending failure due to pipe wall thinning or to reliably track wear rates.

Pipe Wear Trend Monitoring

A demonstration of the ability to monitor and quantify the wear rates in a pipeline has been demonstrated in the field. In FIG. 20, the wear rate in a high wear rate environment shows the rapid decrease of wall thickness over a period of 23 weeks.

Pipe Surface, Thermal Cycling and Long Term Elevated Temperature Effects

Figure 21A:
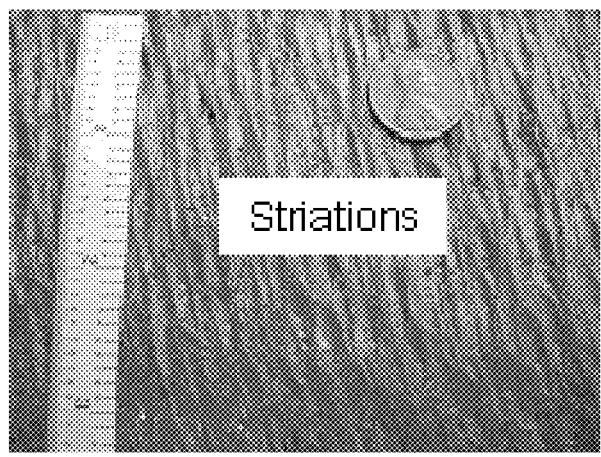
FIGS. 21a, 21b and 21c, show inner surface irregularities seen on a chromium-steel worn pipe.
Figure 21B:
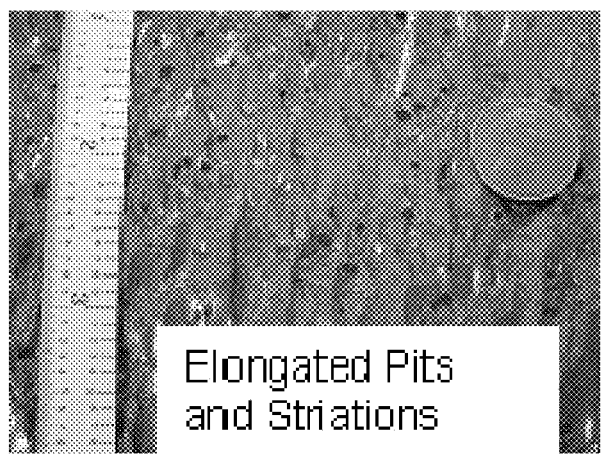
Figure 21C:
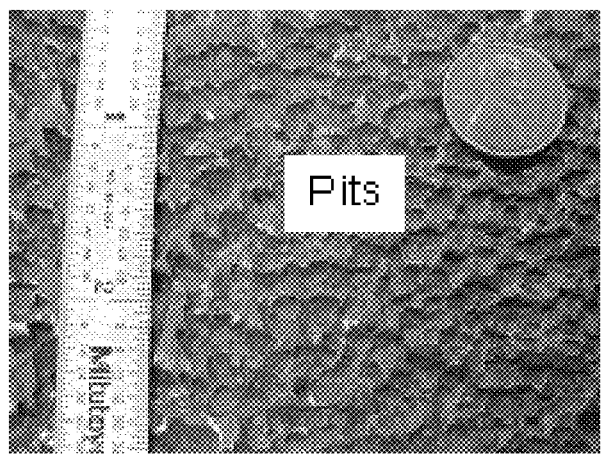

It is to be expected that the inside surface of the pipe will have an impact on the strength and form of the reflected ultrasonic signal. Long term effects including temperature cycles and high temperature degradation will also play a role in the reliability of these measurements. Tests are underway to fully understand the impact of these effects. To date, a variety of pipes from steel to chromium-steel with a variety of inner surface topologies have been studied and tested with good results, as verified with caliper measurements. Three of these surfaces are shown in FIG. 21.

Figure 22A:
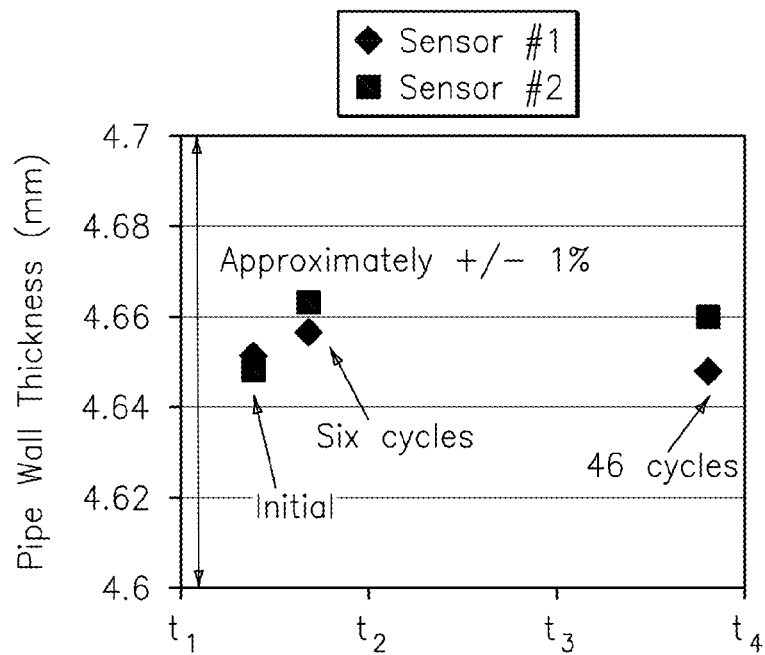
FIG. 22 shows two graphs showing the impart of temperature cycling on wall thickness measurement and signal amplitude (−40 C to +40 C with 10 hour hold), including FIG. 22a which is a graph of pipe wall thickness (mm) versus time (days), where times $t_1$, $t_2$, $t_3$, $t_4$ are about 25 days apart, and FIG. 22b which is a graph of signal level versus microseconds.
Figure 22B:
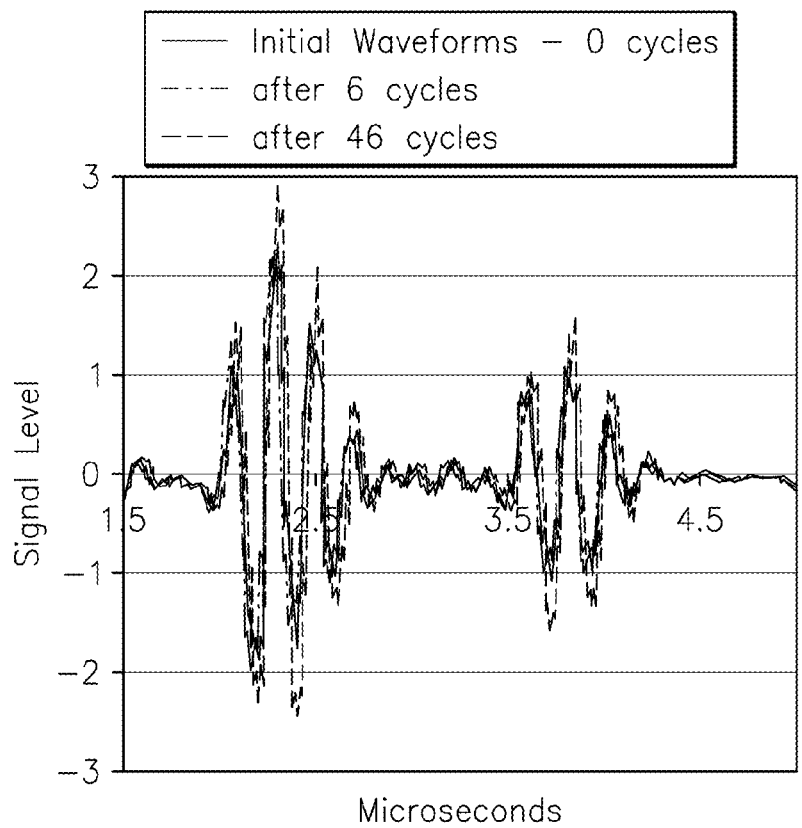
Figure 24:
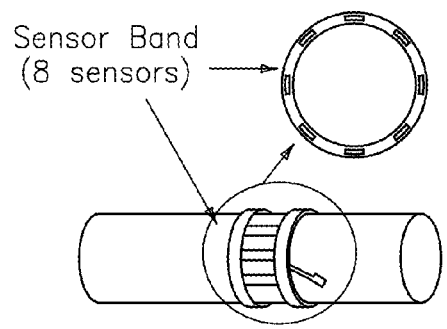
FIG. 24 is an illustration of a pipe having a sensor according to the present invention.

Temperature cycling from −40 C to +40 C with 10 hour holds on a semi-permanent style system using ultrasonic gel couplant has been initiated and the results of the first 46 thermal cycles reveals no discernable difference in pipe wall thickness as seen in FIG. 22. In addition, a comparison of the amplitudes of the signals from one of the sensors indicated no degradation in amplitude as seen in FIG. 22. After 46 cycles, the amplitude of the signal increased relative to the initial pulse and the pulse after 6 cycles.

The long term testing at 50 C to 70 C showed no detectable change in the pipe wall thickness measurement, that is no detectable change in the time from the initiation of the trigger pulse to the detection of the reflected ultrasonic signal. The amplitude of the signal which has a bearing on the reliability of the sensing system and the signal to noise did show some slight degradation of less than 20% amplitude over a period of three months as seen in FIG. 23. A new design has been implemented which is expected to see much lower amplitude changes in the ultrasonic signals during similar long term testing. In addition, a permanent style system which does not use ultrasonic gel couplant is expected to see even smaller changes.

FIGS. 24-28

Other Pipe Wall Thickness Measurement Systems and Improvements

A common problem for pipelines of all types is the potential for corrosion and wear of the pipes inner surfaces over time and the potential for pipeline rupture if the wall becomes too thin. The corrosion or wear in applications such as slurry transport is so severe that in some instances pipes have to be replaced several times a year. In some applications where the wear and corrosion is not uniform (i.e. more wear on the bottom inside of the pipe) the pipes are frequently rotated to even out the wear and increase the overall lifetime of the pipe.

Pipe Wall Thickness Measurement System with Self-Referencing Measurements and Pipe Orientation Correction Currently, pipeline operators monitor the condition of the walls of their pipes using handheld ultrasonic gauges that must be placed in contact with the pipe for each measurement point. This process has to be repeated for multiple points at the same pipe location since the entire circumferential profile of the pipe is desired. This is a very time consuming and error prone process performed on frequently a large number of measurement locations, sometimes numbering up into the tens of thousands of points. Permanent attachment of the ultrasonic sensors would improve the reliability of the measurements, but this approach is not practical or cost effective particularly in the applications that require frequent pipe rotations or replacement.

The present invention provides a new measurement system that is based on the same basic ultrasonic measurement principle but presents a novel approach that eliminates many of the current problems. The basic sensing transducer is a series of piezoelectric elements (such as PVDF) that are permanently attached to the pipe wall. See FIG. 24. As shown here, the sensors are equally spaced circumferentially around the pipe to provide a complete profile of the wall thickness. However the spacing or number of sensors does not have to be fixed.

Since piezo elements made of materials like PVDF are cheap, the sensor band can be permanently attached providing for very reliable and repeatable measurements. The electronic reading unit can be portable and hand carried to the sensor bands or permanently mounted next to the sensor band, collecting data and storing or relaying the data by wireless or other means to a central gathering station.

Measurement of the wall thickness will be performed by the well known single element pitch-catch method, where the PVDF serves as both the ultrasonic signal transmitter and receiver (alternatively 2 PVDF elements could be used in a dual-transducer approach). An ultrasonic pulse is injected into the pipe by way of the PVDF sensor; the pulse then reflects off the back surface of the pipe wall and is detected by the same PVDF sensor. The amount of time it takes for the received pulse to traverse the pipe wall is proportional to 2 times the wall thickness. However it is often difficult to achieve the required accuracy with this single reflection approach since the electronics must inject a large signal into the pipe and then be sensitive enough to detect rapidly a respectively weak return pulse. This must be accomplished with very precise timing to obtain an accurate thickness measurement.

Figure 25A:
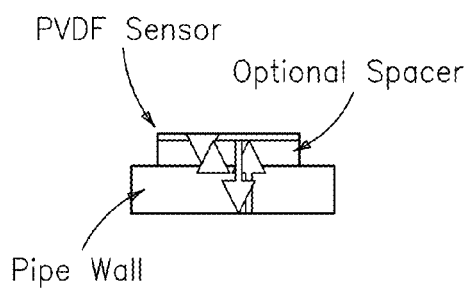
FIGS. 25a and 25b, shows two embodiments of the present invention having an optional spacer arranged between the pipe wall.
Figure 25B:
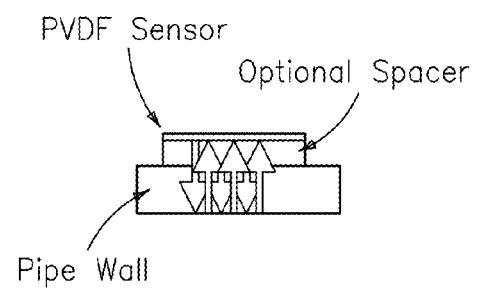
Figure 26:
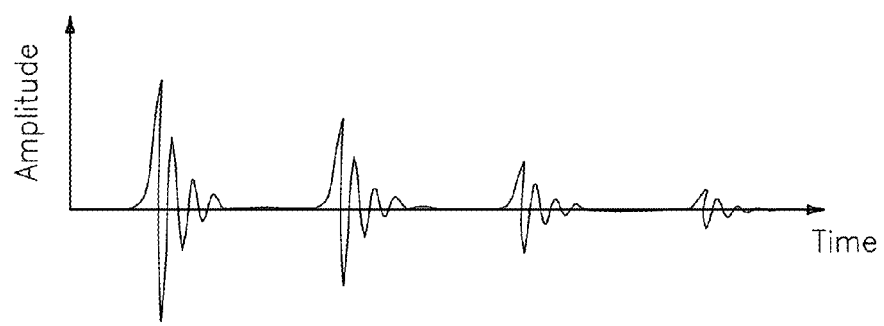
FIG. 26 is a graph of signal amplitude versus time of a pulse injected into a pipe wall and bouncing back-and-forth.

This disclosure utilizes a self-referencing approach that will greatly improve the accuracy. FIG. 25 shows two implementation. In a), once the pulse is produced it is injected into a spacer and from there it travels to the pipe wall. Once the pulse hits the outer pipe wall an amount will be reflected back, along with the reflection from the inner pipe wall a certain time later. The difference between these two detected pulses is proportional to the wall thickness. In addition, as shown in b), the injected pulse into the pipe wall will continue to bounce back-and-forth producing a series of equally spaced pulses as shown in the data in FIG. 26. To determine the wall thickness the time between successive pulses is measured, eliminating the requirement for absolute timing based on the injected pulse. The received pulses can be detected with a variety of signal processing techniques ranging from simple peak detection to quadrature, homodyne or heterodyne demodulation.

One unique problem arises in applications where the pipes are frequently rotated to equalize the inside wear and prolong the lifetime of the pipe. In these systems the wall thickness data that is obtained is used to try and predict both the rotation schedule of the pipe along with the replacement schedule. In the case of the band sensor system presented here, since only discrete points are measured (not continuously) algorithms will be utilized to interpolate between the sensors to obtain a fully continuous wall thickness prediction. To accurately predict the pipe future condition and somewhat interpolate between sensors, the pipe orientation must be known. This information will be used to calculate variable wear rates at different positions on the pipe due to, for example, heavier materials traveling along the bottom of the pipe and inducing greater wear in that location. The orientation of the pipe can be recorded through relative markings placed on the pipe and band; however this system is prone to recording errors. Instead a system proposed here utilizes simple and cheap 2D orientation sensors to automatically record and orient the data. 2 or 3 of these sensors spaced along the band and around the pipe will be able to accurately provide orientation data. Multiple sensors will allow refinement of the semi-accurate data provided by the cheap sensors to pinpoint the orientation.

The system described here represents a cheap way to quickly obtain reliable pipe wall thickness data. The sensor band is optimized on low cost so that it can be permanently attached to the pipe and thrown away when the pipe is worn out. It is a low profile device that can be placed under insulation or other pipe coverings and rotated with the pipe in applications where pipe rotation is required.

The wall thickness and pipe orientation data provided by the system can greatly optimize the operation of pipelines both in the respects of minimizing pipe ruptures as well as helping to prolong the lifetime of the pipes through optimization of pipe rotation and replacement.

Pipe Wall Thickness Measurements with Large Area Sensors

Figure 27A:
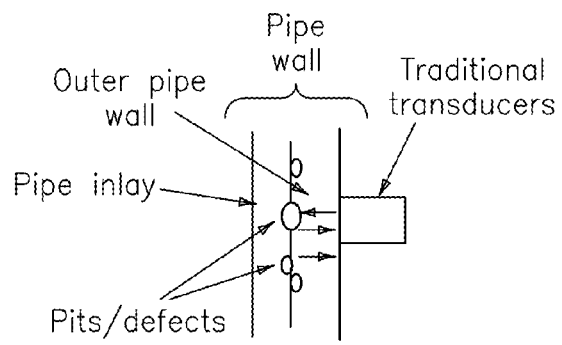
FIGS. 27a and 27b, shows embodiments of the present invention using a traditional ultrasonic transducer and a PVDF large area ultrasonic transducer.
Figure 27B:
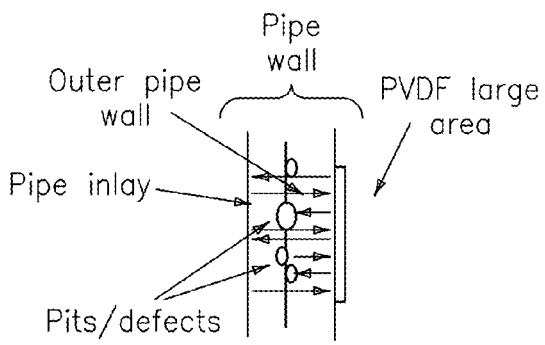

When measuring pipe wall thickness with traditional ultrasonic transducers, the system can often be confused when small area defects or pits are present in the pipe wall. This condition can often be found in specialty lined pipes that are used in harsh wear environments. Fedur and chromium-lined pipes are typical examples. In the case of chromium lines pipes, a standard carbon-steel pipe is taken and a bead of chromium is welded in a spiral fashion inside the standard pipe, providing a solid inlay. This pipe demonstrates improved wear characteristics; however the welding process will create a large number of small voids, bubbles and defects at the interface layer between the chromium and the outer carbon-steel. When a wall thickness measurement is made on this pipe the defects and voids will reflect the ultrasonic energy that strikes them, potentially giving a false thickness measurement. FIG. 27a) shows a diagram of how this may occur. The smaller focused beam of the traditional ultrasonic sensors may hit a defect or a small cluster of defects and reflect back enough energy to give a false reading. Often times the transducer can be slightly moved to clear the small obstruction, but an operator will not know this needs to be done.

The present invention provides an advantage of a PVDF based pipe wall thickness measurement that helps to remedy this problem. This can be accomplished since a PVDF ultrasonic sensor can be fashioned easily in a variety of shapes and sizes. For typical inlayed pipe the small defects are present at the interface between the two layers in a relatively even distribution, however the majority of the interface area is clear of defects. By using a PVDF sensor which is spread out over a large area, a large area ultrasonic beam is introduced into the pipe wall. The defects will reflect back a portion of the ultrasonics signal, however a large portion of the signal will still travel through and be reflected back by the true pipe inner wall. The received signal will exhibit a small amplitude when the defect reflected signal are detected, however a large signal will be observed from the inner pipe wall. Now, both the amount of defects can be seen along with the true inner pipe wall thickness.

Several methods can be used to process the resulting signals to discern the defect signals from the inner wall signals.

The most telling signal is simply the amplitude. Since the defects are plentiful in a typical lined pipe however do not cover the majority of the area they will give a smaller reflected profile.

Permanent Pipe Wall Monitoring System with
Disposable Sensor Elements

Current pipe wall thickness measurements are performed with hand held thickness transducers and electronics. This requires a manual attachment of the sensor transducer to the pipe each time a measurement is desired, resulting poor repeatability and accuracy. The quality of the data obtained is very dependent on the skill, training and experience of the operator. They system described here replaces the manual pipe wall thickness measurements with a permanently mounted system that will improve repeatability and accuracy.

Figure 28A:
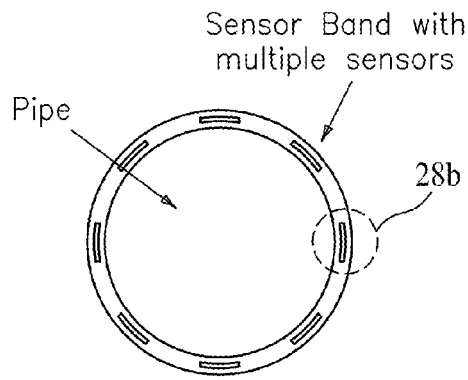
FIGS. 28a and 28b, shows embodiments of the present invention using either a couplant between a pipe wall and a PDVF sensor, or a compliant backing material between the PDVF sensor and a band, or a combination thereof.

In its simplest form the sensor head consists of a ring of multiple sensors that are permanently attached to the outside of the pipe to be measured. FIG. 28a shows a configuration here the light areas represent the actual sensors.

Figure 28B:
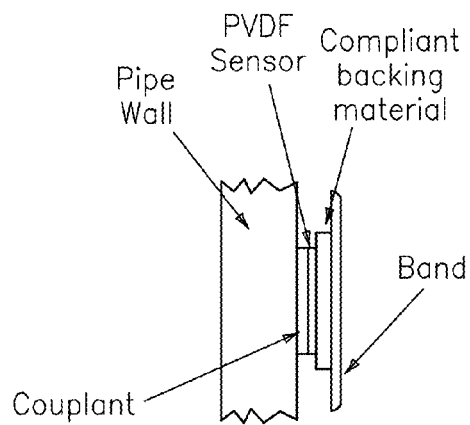

To achieve the low cost and flexibility required a piezoelectric (PZT) material PVDF is used for the sensors. Since PVDF is not as sensitive as the traditional PZT materials for wall thickness measurements it is important that the PVDF sensors be placed in as close a contact with the pipe wall as possible. In FIG. 28b a samples and construction is shown, this construction has the advantage of protecting the sensitive PVDF material while also providing the best ultrasonic signal pathway from the sensor to the pipe wall. In this example, a rugged band is used to compress the sensors onto the outside of the pipe. This band can be made of metal which will impart a compressive force to maintain contact between the sensors and the pipe while also providing the environmental protection. Under the band a piece of compliant material (such as rubber) is attached at the sensor locations. This compliant material is used to cushion the PVDF but to also allow the PVDF to conform to the shape of the surface of the pipe. Since the outer surface of the pipe may contain ridges or steps in its surface it is advantageous to force the PVDF to conform to the shape as much as possible. This will maximize the amount of signal the sensor will receive from the pipe wall and improve overall system performance. Under the sensor a couplant is used to help transfer the ultrasonic energy from the sensor to the pipe and vice versa during the measurement. This couplant can take the form of a solid gel, a liquid gel or a combination of the two. The goal of the gel is to eliminate all air pockets on the pipe surface and maximize the ultrasonic signal path between the sensors and the pipe wall. The liquid gel will serve to fill the voids, however often the gel will dry out over time. The solid gel typically will not be able to get down into all the voids. However, a combination of the two with the liquid gel in the smallest voids, covered over by the solid gel should provide a good long lasting ultrasonic path.

FIG. 29

Measurement and Visualization of Pipe Wear

As shown in FIG. 29, and consistent with that described above, the pipe wall thickness measurements can be graphed in a polar plot to provide a visual indication of the wall thickness as a function of the angular distance from the top of the pipe. A set of representative plots from data taken at a customer site clearly shows high wear rates on the pipes as seen in FIG. 29. The degree of wear is unequivocally seen. In the plot shown in FIG. 29a the high wear rate is on the bottom of the pipe as expected in a stratified (non-homogeneous) flow situation. In FIG. 29b, the high wear rate appears to be on the top of the pipe due to an intentional rotation of the pipe performed to increase pipe lifetimes. In other situations, uneven pipe wear will result from changes in the flow profile after elbows or other pipe geometry effects.

FIGS. 30-32

Pipe Wall Thickness Interpolation and Wear
Extrapolation

The system according to the present invention is designed to be permanently attached to a pipe and provide, e.g., 12 discrete pipe wall thickness measurements, although the scope of the invention is not intended to be limited to any specific number of sensors or measurements. Since the sensors are permanently attached the system provides a very reliable and repeatable thickness measurement in the exact same location. In addition, the 12 sensors are equally spaced circumferentially around the pipe. The combination of the high quality measurements and spatial placement permits insight into additional information on the condition of the pipe as well as accurate predictions into the future pipe wear.

Figure 30:
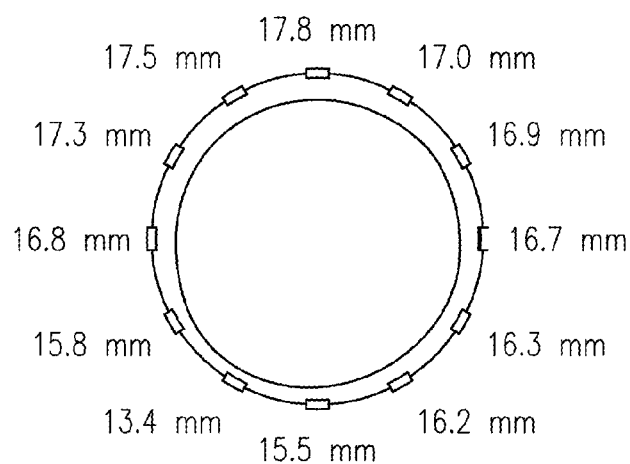
Figure 31:
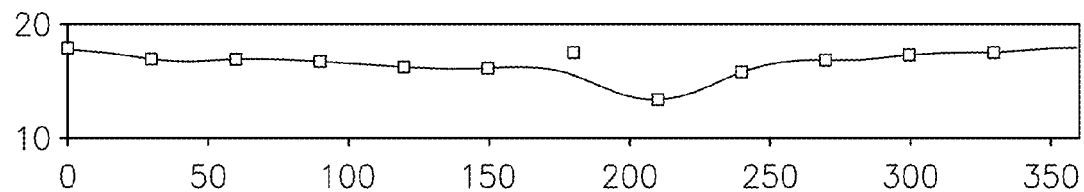
FIG. 31 is a graph of a measured wall thickness versus angular position about a pipe, showing a case where measured wall thickness cannot be described by a set of limited Fourier components.

FIG. 30 shows an example of the 12 circumferential points. Several methods can be used to interpolate in between the individual 12 measured pipe wall thicknesses. Cubic spline or polynomial regression techniques are two examples of curve fitting routines that can provide interpolated points. However, due to the periodic and repeating nature of the equally spaced points measured around the circumference of the pipe, a Fourier decomposition based interpolation is ideal. This technique calculates the various Fourier components required to create a curve which includes all the sample points. Once the equation of the curve is known that includes the 12 measured points the intermediate locations between the points can be calculated. Using this interpolation the minimum wall thickness can be found, even if the minimum thickness point is between the actual measured locations. An additional benefit of this analysis is that erroneous sensor readings can potentially be identified. A sensor reading that is far off will either not permit the Fourier decomposition to converge on a solution, or will require an excessively large high frequency component. By limiting the magnitudes of the various derived Fourier components to physically realistic values points that cannot be described with the derived Fourier components can be flagged as potential erroneous points. In addition, custom tailored weighting coefficients can be used on the Fourier components depending on the particular situation. FIG. 31 shows a situation where a measured wall thickness cannot be described by a set of limited Fourier components. Here the wall thickness (y-axis) versus degree rotation (x-axis) around the pipes is shown. The squares represent the measured values and the line the interpolated numbers. In this particular situation the highest frequency component would have been the largest component if the Fourier decomposition was allowed to fit to all points. By limiting the magnitude of this component the point at 180 degrees is identified and discarded from the data set.

Figure 32:
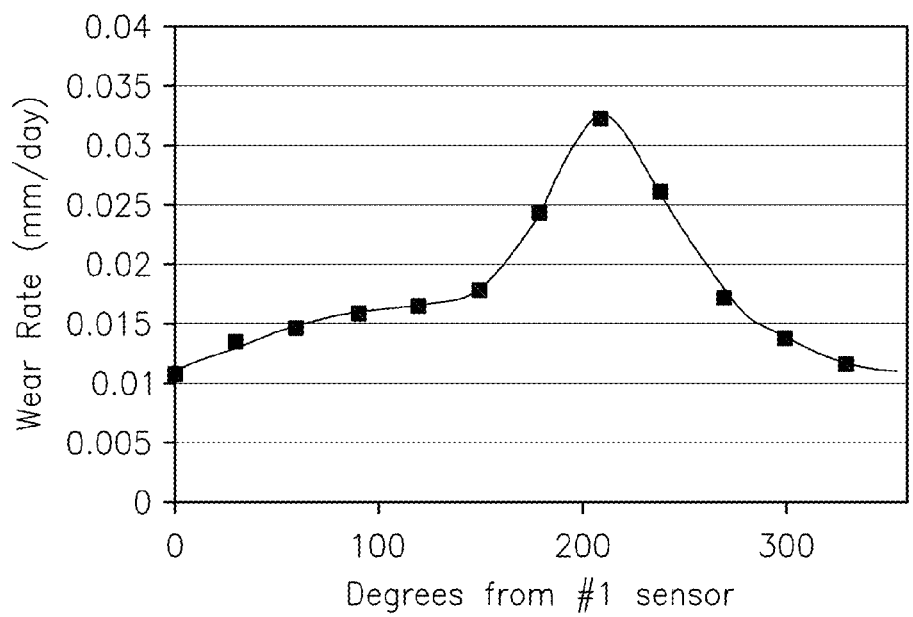
FIG. 32 is a graph of a wear rate (mm/day) versus degrees from a sensor showing a calculated wear model for a pipe.

In addition to interpolation between the measured points of the wall thickness, analysis can be used to predict the future condition of the pipe. From the frequent accumulation of data and the accuracy of the data, extrapolation techniques can be used to model and predict the future pipe wear. FIG. 32 shows an example of a calculated wear model for a pipe. Several techniques can be used to derive the wear profile and extrapolate the future pipe wall thickness including least-square polynomial extrapolation and Fourier component extrapolation. The scope of the invention is not intended to be limited to any particular type or kind of extrapolation technique, and embodiments are envisioned using other types or kinds of extrapolation techniques either now known or later developed in the future.

The techniques described here permit additional pipe information to be obtained from the measurement of pipe wall thickness using the present technology. Whole pipe interpolation permits the monitoring of pipe wall thicknesses throughout the full circumference of the pipe with only 12 actual measurements. In addition, future pipe condition can be extrapolated by calculating a wear profile and determining the ideal lifetime or rotation schedules for the pipe to optimize the pipe viable life. The model can help determine when a pipe should be rotated and at which angles in an effort to equally distribute the pipe wear around the pipe inner wall. Also trigger points can be established such that the model will predict certain wall thickness configurations requiring intervention from maintenance personnel.

FIG. 33

Adaptive Frequency Tuning for Pipe Wall Thickness Measurements

The measurement of material thicknesses using ultrasonic techniques is well known. The most prevalent method involves a simple pulse-receive time based approach that measures the amount of time it takes for an ultrasonic pulse to traverse the material thickness. Often this measurement is performed with the ultrasonic transmitter & receiver located essentially in the same location. Therefore the ultrasonic pulse must travel through the material, bounce off the opposite side and then return to be detected. Along the path the ultrasonic signal must travel, several mechanisms can attenuate the signal and possible severely degrade the measurement or prevent a measurement from being taken. This disclosure discussed a technique to aid in the maximization of the signal received as well as a means for continuously maintaining the signal integrity.

Figure 33:
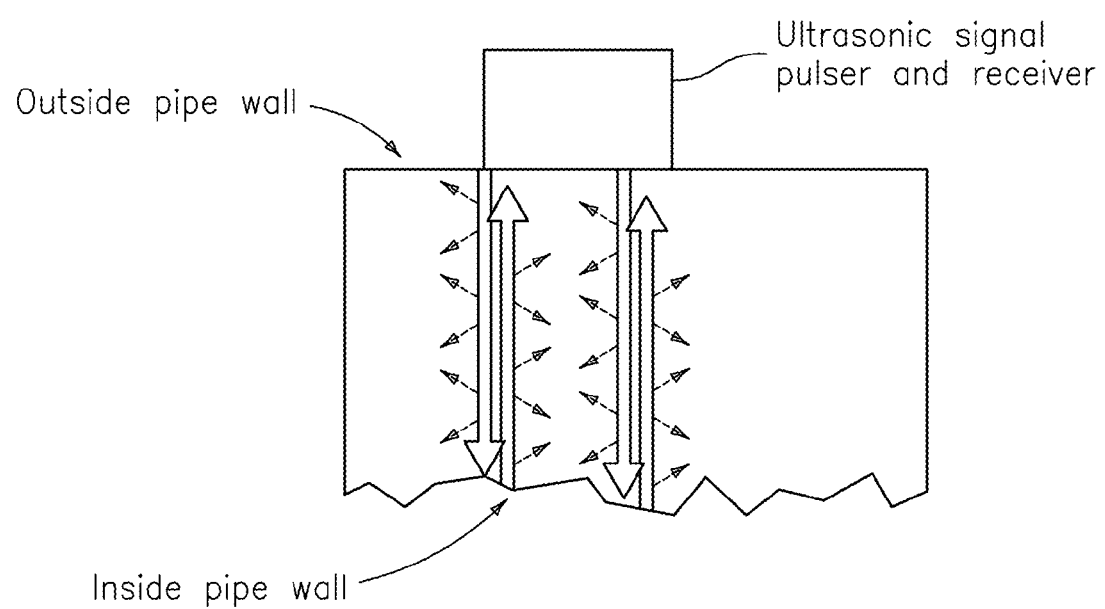
FIG. 33 is a diagram of a path of a an ultrasonic signal through the material of a pipe wall.

As the ultrasonic signal traverses through the material under test and reflects off the opposing side it is subject to several mechanisms including attenuation of the material and surface interferences from the reflecting side. FIG. 33 shows a diagram of the path of the ultrasonic signal through the material and these two key attenuation mechanisms.

These two key items can be potentially minimized significantly by tuning the frequency of the ultrasonic pulse used to probe the material.

The attenuation of acoustic waves varies with frequency and often can exhibit large variations with the doubling or tripling of the frequency; therefore by simply optimizing the ultrasonic frequency large gains in resultant signals amplitude can be achieved. With traditional ultrasonic transducers based on ceramic piezoelectric elements the tuning frequency is often very limited. These materials typically exhibit a sharp resonance peak and their efficiency quickly drops off once they are de-tuned. PVDF and some other materials however exhibit more of a broad-band response. These materials are much more conducive to frequency tuning and laboratory testing has demonstrated that they can indeed be frequency tuned to minimize the effects of the subject materials attenuation characteristics.

The reflection of the ultrasonic signal off the opposing wall of the material as shown in FIG. 33 imposes two mechanisms that effect the quality of the signal reaching the ultrasonic receiver. First, irregularities in the signal will cause portions of the injected signal to reflect off in different angles, reducing the returned signal. In addition, since the surface of the inner wall can vary within the area of the ultrasonic signals portions of the signal will travel slightly different distances when it recombines at the sensor. This can result in interference of the signal with itself, and in the case of destructive interference will reduce the measured signal. The frequency of the ultrasonic signal can vary both of these effects and can be used to minimize their effects. As an example, in general a lower frequency signal (and therefore a longer wavelength) will not be as susceptible to small surface variations in relation to the signal wavelength.

In addition, with an adjustable frequency of the ultrasonic signal advanced signal processing techniques can be utilized to reduce the signal-to-noise of the detected signal. Synchronous detection of a phase or frequency encoded radio signal has been used extensively to improve radio reception. These same techniques can be utilized to improve the signal integrity of the ultrasonic signals. By modulating the phase of the ultrasonic signal with, for example, an m-sequence code, a demodulator on the receive side could correlate with the known code and be able to detect the desired signal from system noise and other non-coherent reflections.

FIG. 34

The Orientation or Rotation Sensor

Figure 34:
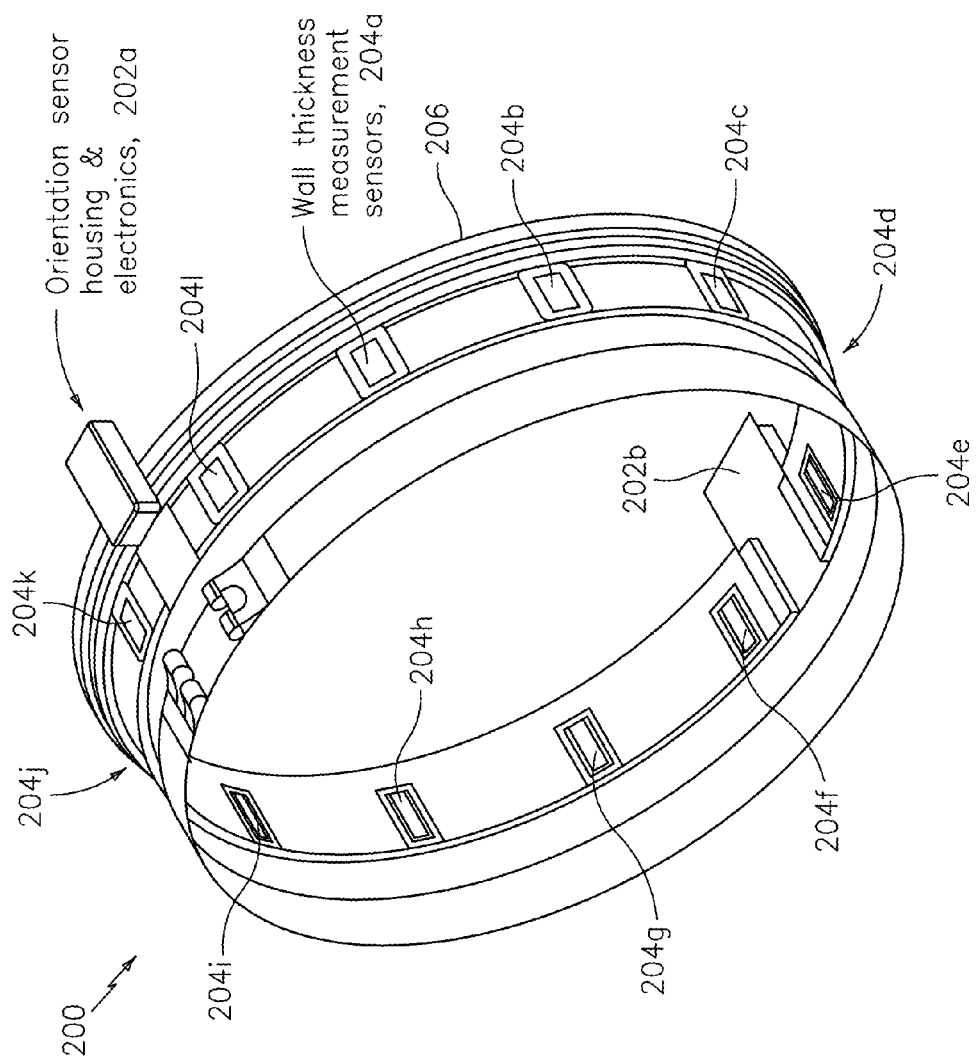
FIG. 34 shows an embodiment in which an orientation or rotation sensor is integrated into a sensor board along with the pipe wall thickness measurement devices.

FIG. 34 shows an embodiment generally indicated as 200 of the apparatus or system of the present invention in which one or more orientation or rotation sensors 202a, 202b is integrated along with the multiple wall thickness measurements indicated as 204a, 204b, 204c, . . . , 204k, 204l into a sensor band 206. The orientation or rotation sensors 202 is shown as a device having an orientation sensor housing and electronics that is arranged in the sensor band 206 in relation to the multiple wall thickness measurements 204a, 204b, 204c, . . . , 204k, 204l. As shown, the sensor band 206 has two orientation or rotation sensors 202a, 202b, one arranged at the top 202a, and one arranged at the bottom 202b, although the scope of the invention is not intended to be limited to the number or angular position of the same in the sensor band 206. As a person skilled in the art would appreciate, when the wall thickness measurements 204a, 204b, 204c, . . . , 204k, 204l are arranged circumferentially equi-distantly about the sensor band 206 in relation to the one or more orientation or rotation sensors 202a, 202b, then the orientation of each wall thickness measurements 204a, 204b, 204c, . . . , 204k, 204l may be determined based on the orientation the one or more orientation or rotation sensors 202a, 202b. The orientation is understood to be in terms of the angular position of the orientation or rotation sensor from 0 to 360 degrees about the circumference of the pipe. In operation, each orientation or rotation sensor 202a, 202b responds to its orientation after the sensor band 206 is arranged on the pipe (not shown), and provides an orientation signal containing information about its angular position about the pipe, e.g., back to the one or more modules 102a.

One problem that the customer faces is that they do not have an accurate tracking of the pipe orientation along with the wall thickness data. With the integration of the orientation or rotation sensor 202a, 202b, one now will know the current pipe orientation along with very repeatable thickness measurements. This allows the technique according to the present invention to not only report this to the customer, but opens up the possibility of enhanced future pipe predictive behavior.

As an example for a very striated flow in the pipe (i.e. where the heavy sand and rock laden material is flowing along the bottom of the pipe, relative to the water rich portion at the top), the technique according to the present invention can estimate the pipe wear rate at the top versus the bottom. The technique according to the present invention can then may predict the lifetime of the pipe and optimize customer pipe rotation schedules. The orientation rotation or sensor 202a, 202b is the key here since it will provide the orientation (i.e. which is at the bottom subject to the high wear).

Orientation rotation or sensors are known in the art; and the scope of the invention is not intended to be limited to any particular type or kind thereof either now known or later developed in the future. By way of example, one known orientation rotation or sensor that has been used takes the form of a gravity-based device that is configured to respond to its orientation, and provides an orientation signal containing information about its angular position.

III. Conclusion

Existing sonar-based flow measurement technology has been extended to two new applications. It has been demonstrated that a sonar-based meter is able to measure the velocity profile in a horizontal slurry line in real-time. Measured changes in the velocity profile show the ability to detect different flow regimes: both homogeneous and heterogeneous flow with fully suspended solid particles, and flow with a stationary bed. The ability to detect a stationary bed was confirmed by separate measurements of density across the bottom of the pipe and differential pressure across the velocity profile meter. One potential benefit of this measurement for hydro transport line operation is reduction of water and energy usage by operating at higher solids concentration and/or lower velocities while avoiding problems and costs due to solids deposition.

The ability to reliably, accurately, and cost effectively provide pipe wall thickness measurements in a timely manner has been demonstrated. The repeatability over a variety of operating conditions including sensor to sensor variation, temperature ranges, and time has been clearly shown in both laboratory and field tests. This technology is easily extended into monitoring of most structures found in a pipeline including elbows, valves, and many others. The resulting cost savings for both the pipe inspections and production savings through enhanced production up-time can be quite large. Most importantly, the potential impact on personnel safety and environmental savings will be enormous.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

The invention claimed is:

1. Apparatus for determining a thickness of a wall of a pipe, characterised in that the apparatus comprises:

a signal processing module configured to respond to signaling containing information about traveling stress waves transmitted to and reflected back from an inner surface and an outer surface of a wall of a pipe by a sensor band that includes a series, ring or array having multiple PVDF transducers circumferentially arranged at angular positions and mounted around, and attached to or clamped onto, the outer surface of the wall of the pipe, the signaling being generated over a period of time by each of the multiple PVDF transducers in the sensor band that transmits respective traveling stress waves and senses reflections of the traveling stress waves transmitted that are reflected back from the inner surface a certain time later than from the outer surface at each circumferential location of a respective one of the multiple PVDF transducers; and determine corresponding signaling containing information about a time-based trending profile of a thickness of the wall of the pipe corresponding to respective circumferential locations of the multiple PVDF transducers as a function of the angular position and the period of time, based on the signaling received from the sensor band using a self-reference approach where the difference in time between the reflections of the traveling stress waves being reflected back from the inner surface and the outer surface is proportional to the thickness of the wall of the pipe; and one or more orientation or rotation sensors, each responding to its orientation in relation to its displacement on the pipe and to provide an orientation signal containing information about the same.

2. Apparatus according to claim 1, wherein the one or more orientation or rotation sensors provides the orientation signal back to the signal processing module.

3. Apparatus according to claim 1, wherein the signal processing module is configured to receive the orientation signaling containing information about an angular position of at least one orientation sensor arranged on the pipe.

4. Apparatus according to claim 1, wherein the signal processing module is configured to receive and use the orientation signaling to calculate variable wear rates at different positions on the pipe, based at least partly on the fact that heavier materials tend to travel along the bottom of the pipe and induce greater wear in that location.

5. Apparatus according to claim 1, wherein the one or more orientation or rotation sensors comprise at least two orientation or rotation sensors spaced along the sensor band and around the pipe to provide orientation data.

6. Apparatus according to claim 1, wherein the signal processing module is configured to receive and use the orientation signaling to predict a pipe future condition, based at least partly on the orientation signal received.

7. Apparatus according to claim 1, wherein the signal processing module makes the determination based at least partly on the time traveling stress waves travel to and are reflected back from the inner surface and outer surface of the wall of the pipe.

8. Apparatus according to claim 1, wherein the signal processing module provides corresponding signaling containing information about the time-based trending profile of the thickness of the wall of the pipe.

9. Apparatus according to claim 8, wherein the corresponding signaling contains information about a graph to provide a visual indication of the thickness of the wall of the pipe.

10. Apparatus according to claim 9, wherein the graph is a polar plot that provides the thickness of the wall of the pipe as a function of the angular distance from a set reference point of the pipe.

11. Apparatus according to claim 1, wherein the signal processing module provides an input signal to the multiple PVDF transducers.

12. Apparatus according to claim 1, wherein at least one transducer PVDF propagates a respective traveling stress wave through the wall of the pipe.

13. Apparatus according to claim 1, wherein the apparatus comprises the sensor band that includes the series, ring or array of the multiple PVDF transducers that are permanently or semi-permanently mounted around, attached to or clamped onto, the outer surface of the wall of the pipe.

14. Apparatus according to claim 1, wherein each of the multiple PVDF transducers responds to an input signal from the signal processing module and provides a respective traveling stress wave that is propagated through the wall of the pipe.

15. Apparatus according to claim 1, wherein each PVDF transducer responds to respective traveling stress waves reflected off the inner surface and the outer surface of the wall of the pipe and returned back to said each PVDF transducer, and provides a respective output signal containing information about the same that can be used to determine the thickness of the wall of the pipe.

16. Apparatus according to claim 1, wherein the signal processing module is configure to determine the thickness of the wall of a steel pipe or a polymer pipe.

17. Apparatus according to claim 1, wherein the signal processing module is configured to determine an absolute thickness of the wall of the pipe.

18. Apparatus according to claim 1, wherein the signal processing module is configured to determine a relative thickness of the wall of the pipe, based at least partly on a pipe wall thickness trend that includes at least one comparison of the thickness of the wall of the pipe performed at two different periods of time.

19. Apparatus according to claim 1, wherein the signal processing module determines an interpolation of the thickness of the wall of the pipe between one or more pairs of sensor points in the series, ring or array of the multiple PVDF transducers.

20. Apparatus according to claim 1, wherein the multiple PVDF transducers comprise piezoelectric elements.

21. Apparatus according to claim 1, wherein the multiple PVDF transducers are equally spaced circumferentially around the outer surface of the wall of the pipe so as to provide a complete profile of the thickness of the wall of the pipe.

22. Apparatus according to claim 1, wherein at least one PVDF transducer is an ultrasonic signal transmitter and receiver that receives an input signal from the signal processing module, and provides the signaling containing information about the traveling stress waves transmitted to and reflected back from the wall of the pipe.

23. Apparatus according to claim 1, wherein the signal processing module determines a substantially continuous wall thickness prediction around the wall of the pipe.

24. Apparatus according to claim 1, wherein the signal processing module makes the determination based on an orientation of the sensor band around the outer surface of the wall of the pipe.

25. Apparatus according to claim 24, wherein the signal processing module makes the determination based on a recordation of data related to the orientation of the sensor band around the outer surface of the wall of the pipe.

26. Apparatus according to claim 1, wherein the time-based trending profile is a complete profile corresponding to the multiple PVDF transducers circumferentially arranged around the outer surface of the wall of the pipe.

27. Apparatus according to claim 1, wherein the signal processing module determines a future pipe condition prediction by an extrapolation technique, based at least partly determining a calculated wear model or profile using some combination of a least-square polynomial extrapolation and Fourier component extrapolation.

28. Apparatus according to claim 1, wherein the signal processing module determines a lifetime schedule or a rotation schedule for the pipe, based at least partly on either when or at which angle the pipe should be rotated so as to distribute substantially equally the wear of the pipe around the inner wall of the pipe.

29. Apparatus according to claim 1, wherein the signal processing module determines trigger points that can be used to predict certain wall thickness configurations requiring intervention from maintenance personnel.

30. Apparatus according to claim 1, wherein the period of time is measured in weeks or months.

31. Apparatus according to claim 1, wherein the corresponding signaling includes a plurality of respective time-based profiles determined during the period of time.

* * * * *